(12) United States Patent
Auer et al.

(10) Patent No.: US 11,680,110 B2
(45) Date of Patent: Jun. 20, 2023

(54) THREE-DIMENSIONAL STRUCTURE-BASED HUMANIZATION METHOD

(71) Applicant: Hoffmann-La Roche Inc., Little Falls, NJ (US)

(72) Inventors: Johannes Auer, Schwaigen (DE); Guy Georges, Habach (DE); Stefan Klostermann, Neuried (DE); Wolfgang Schaefer, Mannheim (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 599 days.

(21) Appl. No.: 16/633,423

(22) PCT Filed: Jul. 27, 2018

(86) PCT No.: PCT/EP2018/070372
§ 371 (c)(1),
(2) Date: Jan. 23, 2020

(87) PCT Pub. No.: WO2019/025299
PCT Pub. Date: Feb. 7, 2019

(65) Prior Publication Data
US 2020/0223945 A1    Jul. 16, 2020

(30) Foreign Application Priority Data

Jul. 31, 2017 (EP) .................................... 17183933

(51) Int. Cl.
| C07K 16/46 | (2006.01) |
| C07K 16/24 | (2006.01) |
| C07K 16/28 | (2006.01) |

(52) U.S. Cl.
CPC .......... C07K 16/464 (2013.01); C07K 16/244 (2013.01); C07K 16/2866 (2013.01); *C07K 2317/24* (2013.01); *C07K 2317/565* (2013.01)

(58) Field of Classification Search
CPC ............................ C07K 16/464; C07K 16/244; C07K 16/2866; C07K 2317/24; C07K 2317/565
See application file for complete search history.

(56) References Cited

U.S. PATENT DOCUMENTS

| 5,859,205 A | 1/1999 | Adair et al. |
| 2003/0229208 A1 | 12/2003 | Queen et al. |
| 2006/0258852 A1 | 11/2006 | Lugovskoy et al. |
| 2008/0050357 A1 | 2/2008 | Gustafsson et al. |

FOREIGN PATENT DOCUMENTS

| WO | 2004006955 A1 | 1/2004 |
| WO | 2005061540 A2 | 7/2005 |
| WO | 2008144757 A1 | 11/2008 |
| WO | 2014100542 A1 | 6/2014 |
| WO | 2016062734 A1 | 4/2016 |

OTHER PUBLICATIONS

Pace et al, FEBS Letters 588 (2014) 2177-2184. (Year: 2014).*
The English translation of the Japanese Office Action, dated Jun. 27, 2022, in the related Japanese Appl. No. 2021-085009.
Olimpieri et al., "Tabhu: tools for antibody humanization," Bioinfomnatics, vol. 31, Issue 3, Feb. 1, 2015, pp. 434-435.
Margreitter et al., "Antibody humanization by molecular dynamics simulations—in-silico guided selection of critical backmutations," J. Mol. Recognit., Jan. 8, 2016, vol. 29, pp. 266-275.
Saldanhaa et al., "A single backmutation in the human kIV framework of a previously unsuccessfully humanized antibody restores the binding activity and increases the secretion in cos cells," Molecular Immunology, Aug. 1999, vol. 36, pp. 709-719.
The International Search Report and Written Opinion, dated Oct. 30, 2018, in the corresponding PCT Appl. No. PCT/EP2018/070372.
David Gareth Williams et al: "Humanising Antibodies by CDR Grafting" In: "Antibody Engineering", Jan. 1, 2010 (Jan. 1, 2010), Springer Berlin Heidelberg, Berlin, Heidelberg, XP055369738.
Alexander Bujotzek et al: "Prediction of VH-VL domain orientation for antibody variable domain modeling", Proteins: Structure, Function, and Bioinformatics, vol. 83, No. 4, Jan. 13, 2015 (Jan. 13, 2015), pp. 681-695, XP055179030.
Yoonjoo Choi et al: "Computationally driven antibody engineering enables simultaneous humanization and thermostabilization", Protein Engineering, Design and Selection, vol. 29, No. 10, Jun. 21, 2016, pp. 419-426, XP055416045.
Jinwoo Leem et al: "ABodyBuilder: Automated antibody structure prediction with data-driven accuracy estimation", MABS, vol. 8, No. 7, Jul. 8, 2016 (Jul. 8, 2016), pp. 1259-1268, XP055416058.
James R. Apgar et al: "Beyond CDR-grafting: Structure-guided humanization of framework and CDR regions of an anti-myostatin antibody", MABS, vol. 8, No. 7, Sep. 13, 2016 (Sep. 13, 2016), pp. 1302-1318, XP055416065.
The English translation of the Japanese Office Action, dated Mar. 24, 2021, in the related Japanese Appl. No. 2020-505165.
Studnicka et al., "Human-engineered monoclonal antibodies retain full specific binding activity by preserving non-CDR complementarity-modulating residues," Protein Engineering, Design and Selection, vol. 7, Issue 6, Jun. 1994, pp. 805-814.
The English translation of the Chinese Office Action, dated Nov. 2, 2022, in the related Chinese Appl. No. 201880048859.6.

* cited by examiner

*Primary Examiner* — Julie Wu
*Assistant Examiner* — Cheom-Gil Cheong

(57) ABSTRACT

Herein is reported a method for the humanization of non-human antibodies using a structure-based scoring matrix. With the scoring matrix it is possible to determine (the requirement for and) the suitability of specific (back)mutations of amino acid residues at defined positions of a selected human germline sequence. The scoring matrix takes into account the topology, the three-dimensional structure and the interactions of the respective residue and change. Thereby the influence on antigen binding of a specific amino acid residue change can be determined.

2 Claims, No Drawings
Specification includes a Sequence Listing.

SEQUENCE LISTING

```
<160> NUMBER OF SEQ ID NOS: 82

<210> SEQ ID NO 1
<211> LENGTH: 122
<212> TYPE: PRT
<213> ORGANISM: Cricetulus migratorius

<400> SEQUENCE: 1

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Thr Thr Ser
            20                  25                  30

Gly Tyr Tyr Trp Thr Trp Ile Arg Gln Phe Pro Gly Lys Lys Leu Glu
        35                  40                  45

Trp Met Gly Tyr Ile Gly Tyr Asn Ser Lys Thr Tyr Tyr Asn Pro Ser
    50                  55                  60

Leu Lys Ser Arg Ile Ser Ile Thr Arg Asp Thr Ser Lys Asn Gln Phe
65                  70                  75                  80

Leu Leu His Leu Asn Ser Val Thr Thr Glu Asp Thr Ala Thr Tyr Tyr
                85                  90                  95

Cys Ala Arg Ser Leu Tyr Gly Gly Tyr Lys Asp Ala Phe Asp Ser Trp
            100                 105                 110

Gly Gln Gly Thr Leu Val Thr Val Ser Ser
        115                 120
```

```
<210> SEQ ID NO 2
<211> LENGTH: 12
<212> TYPE: PRT
<213> ORGANISM: Cricetulus migratorius

<400> SEQUENCE: 2

Gly Phe Ser Ile Thr Thr Ser Gly Tyr Tyr Trp Thr
1               5                   10

<210> SEQ ID NO 3
<211> LENGTH: 16
<212> TYPE: PRT
<213> ORGANISM: Cricetulus migratorius

<400> SEQUENCE: 3

Tyr Ile Gly Tyr Asn Ser Lys Thr Tyr Tyr Asn Pro Ser Leu Lys Ser
1               5                   10                  15

<210> SEQ ID NO 4
<211> LENGTH: 12
<212> TYPE: PRT
<213> ORGANISM: Cricetulus migratorius

<400> SEQUENCE: 4

Ser Leu Tyr Gly Gly Tyr Lys Asp Ala Phe Asp Ser
1               5                   10

<210> SEQ ID NO 5
<211> LENGTH: 107
<212> TYPE: PRT
<213> ORGANISM: Cricetulus migratorius

<400> SEQUENCE: 5

Asp Val Val Leu Thr Gln Thr Pro Ala Thr Leu Ser Ala Ile Pro Gly
1               5                   10                  15

Glu Arg Val Thr Met Thr Cys Lys Ala Ser Gln Ser Ile Gly Thr Ser
            20                  25                  30

Leu His Trp Tyr Gln His Arg Pro Asn Glu Thr Pro Arg Leu Leu Ile
        35                  40                  45

Lys Phe Ala Ser Arg Ser Ile Thr Gly Ile Pro Ser Arg Phe Ser Gly
    50                  55                  60

Ser Gly Ser Gly Thr Asp Phe Thr Leu Gly Ile Asn Asn Leu Glu Ala
65                  70                  75                  80

Glu Asp Phe Ala Ile Tyr Tyr Cys Gln Gln Ser Pro Gly Phe Pro Pro
                85                  90                  95

Thr Phe Gly Ser Gly Thr Lys Leu Glu Ile Asn
            100                 105

<210> SEQ ID NO 6
<211> LENGTH: 11
<212> TYPE: PRT
<213> ORGANISM: Cricetulus migratorius

<400> SEQUENCE: 6

Lys Ala Ser Gln Ser Ile Gly Thr Ser Leu His
1               5                   10

<210> SEQ ID NO 7
<211> LENGTH: 7
<212> TYPE: PRT
<213> ORGANISM: Cricetulus migratorius
```

```
<400> SEQUENCE: 7

Phe Ala Ser Arg Ser Ile Thr
1               5

<210> SEQ ID NO 8
<211> LENGTH: 9
<212> TYPE: PRT
<213> ORGANISM: Cricetulus migratorius

<400> SEQUENCE: 8

Gln Gln Ser Pro Gly Phe Pro Pro Thr
1               5

<210> SEQ ID NO 9
<211> LENGTH: 121
<212> TYPE: PRT
<213> ORGANISM: Mus musculus

<400> SEQUENCE: 9

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Asp Ser Tyr
            20                  25                  30

Gly Val His Trp Val Arg Gln Pro Pro Gly Lys Gly Leu Glu Trp Leu
        35                  40                  45

Val Val Ile Trp Ser Asp Gly Thr Thr Thr Tyr Asn Ser Ala Leu Lys
    50                  55                  60

Ser Arg Leu Ser Ile Thr Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Arg Asp Thr His Tyr Arg Leu Tyr Tyr Tyr Ala Met Asp Tyr Trp Gly
            100                 105                 110

Gln Gly Thr Ser Val Thr Val Ser Ser
        115                 120

<210> SEQ ID NO 10
<211> LENGTH: 19
<212> TYPE: PRT
<213> ORGANISM: Mus musculus

<400> SEQUENCE: 10

Thr Val Ser Gly Phe Ser Leu Thr Ser Tyr Gly Val His Trp Val Arg
1               5                   10                  15

Gln Pro Pro

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ala Ser Gly Phe Ser Leu Asp Ser Tyr Tyr Met Ser Trp Val Arg
1               5                   10                  15

Gln Ala Pro

<210> SEQ ID NO 12
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ala Ser Gly Phe Ser Leu Asp Ser Tyr Tyr Met Ser Trp Val Arg
1               5                   10                  15

Gln Ala Pro

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ala Ser Gly Phe Ser Leu Asp Ser Tyr Gly Met His Trp Val Arg
1               5                   10                  15

Gln Ala Pro

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Val Ser Gly Phe Ser Leu Asp Ser Tyr Tyr Trp Ser Trp Ile Arg
1               5                   10                  15

Gln Pro Pro

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Ser Gly Phe Ser Leu Asp Ser Tyr Gly Val His Trp Val Arg
1               5                   10                  15

Gln Ala Pro

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Ala Ser Gly Phe Ser Leu Asp Ser Tyr Gly Met His Trp Val Arg
1               5                   10                  15

Gln Ala Pro
```

```
<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ala Ser Gly Phe Ser Leu Asp Ser Tyr Gly Val His Trp Val Arg
1               5                   10                  15

Gln Ala Thr

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ala Ser Gly Phe Thr Phe Ser Ser Tyr Gly Val His Trp Val Arg
1               5                   10                  15

Gln Ala Thr

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Val Ser Gly Phe Ser Leu Asp Ser Tyr Gly Val His Trp Val Arg
1               5                   10                  15

Gln Ala Pro

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Val Ser Gly Phe Ser Leu Asp Ser Tyr Gly Val Ser Trp Ile Arg
1               5                   10                  15

Gln Pro Pro

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Val Ser Gly Phe Ser Leu Asp Ser Tyr Gly Val His Trp Val Arg
1               5                   10                  15

Gln Ala Pro
```

```
<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Val Ser Gly Phe Ser Leu Asp Ser Tyr Gly Val Ser Trp Ile Arg
1               5                   10                  15

Gln Pro Pro

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Val Ser Gly Phe Ser Leu Asp Ser Tyr Gly Met His Trp Val Arg
1               5                   10                  15

Gln Ala Pro

<210> SEQ ID NO 24
<211> LENGTH: 19
<212> TYPE: PRT
<213> ORGANISM: Homo sapiens

<400> SEQUENCE: 24

Ala Ala Ser Gly Phe Thr Val Ser Ser Asn Tyr Met Ser Trp Val Arg
1               5                   10                  15

Gln Ala Pro

<210> SEQ ID NO 25
<211> LENGTH: 19
<212> TYPE: PRT
<213> ORGANISM: Homo sapiens

<400> SEQUENCE: 25

Ala Ala Ser Gly Phe Thr Val Ser Ser Asn Tyr Met Ser Trp Val Arg
1               5                   10                  15

Gln Ala Pro

<210> SEQ ID NO 26
<211> LENGTH: 19
<212> TYPE: PRT
<213> ORGANISM: Homo sapiens

<400> SEQUENCE: 26

Ala Ala Ser Gly Phe Thr Phe Ser Ser Tyr Gly Met His Trp Val Arg
1               5                   10                  15

Gln Ala Pro

<210> SEQ ID NO 27
<211> LENGTH: 19
<212> TYPE: PRT
<213> ORGANISM: Homo sapiens

<400> SEQUENCE: 27
```

Thr Val Ser Gly Gly Ser Ile Ser Ser Tyr Tyr Trp Ser Trp Ile Arg
1               5                   10                  15

Gln Pro Pro

<210> SEQ ID NO 28
<211> LENGTH: 19
<212> TYPE: PRT
<213> ORGANISM: Homo sapiens

<400> SEQUENCE: 28

Ala Ala Ser Gly Phe Thr Val Ser Ser Asn Tyr Met Ser Trp Val Arg
1               5                   10                  15

Gln Ala Pro

<210> SEQ ID NO 29
<211> LENGTH: 19
<212> TYPE: PRT
<213> ORGANISM: Homo sapiens

<400> SEQUENCE: 29

Ala Ala Ser Gly Phe Thr Phe Ser Ser Tyr Gly Met His Trp Val Arg
1               5                   10                  15

Gln Ala Pro

<210> SEQ ID NO 30
<211> LENGTH: 19
<212> TYPE: PRT
<213> ORGANISM: Homo sapiens

<400> SEQUENCE: 30

Ala Ala Ser Gly Phe Thr Phe Ser Ser Tyr Asp Met His Trp Val Arg
1               5                   10                  15

Gln Ala Thr

<210> SEQ ID NO 31
<211> LENGTH: 19
<212> TYPE: PRT
<213> ORGANISM: Homo sapiens

<400> SEQUENCE: 31

Ala Ala Ser Gly Phe Thr Phe Ser Ser Tyr Asp Met His Trp Val Arg
1               5                   10                  15

Gln Ala Thr

<210> SEQ ID NO 32
<211> LENGTH: 19
<212> TYPE: PRT
<213> ORGANISM: Homo sapiens

<400> SEQUENCE: 32

Ala Ala Ser Gly Phe Thr Val Ser Ser Asn Tyr Met Ser Trp Val Arg
1               5                   10                  15

Gln Ala Pro

<210> SEQ ID NO 33
<211> LENGTH: 19
<212> TYPE: PRT
<213> ORGANISM: Homo sapiens

<400> SEQUENCE: 33

Thr Val Ser Gly Gly Ser Ile Ser Ser Tyr Tyr Trp Ser Trp Ile Arg

```
1               5                   10                  15

Gln Pro Pro

<210> SEQ ID NO 34
<211> LENGTH: 19
<212> TYPE: PRT
<213> ORGANISM: Homo sapiens

<400> SEQUENCE: 34

Ala Ala Ser Gly Phe Thr Val Ser Ser Asn Tyr Met Ser Trp Val Arg
1               5                   10                  15

Gln Ala Pro

<210> SEQ ID NO 35
<211> LENGTH: 19
<212> TYPE: PRT
<213> ORGANISM: Homo sapiens

<400> SEQUENCE: 35

Thr Val Ser Gly Gly Ser Val Ser Ser Tyr Tyr Trp Ser Trp Ile Arg
1               5                   10                  15

Gln Pro Pro

<210> SEQ ID NO 36
<211> LENGTH: 19
<212> TYPE: PRT
<213> ORGANISM: Homo sapiens

<400> SEQUENCE: 36

Thr Val Ser Gly Phe Ser Leu Ser Asn Met Gly Val Ser Trp Ile Arg
1               5                   10                  15

Gln Pro Pro

<210> SEQ ID NO 37
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Arg Ser Ser Gln Ser Leu Val His Ser Asn Gly Asp Thr Tyr Leu Asn
1               5                   10                  15

Trp Tyr Leu Gln Lys Pro Gly Gln Ser Pro Arg Arg Leu Ile Tyr Lys
                20                  25                  30

Val Ser Asn Arg Asp Ser Gly Val
            35                  40

<210> SEQ ID NO 38
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Arg Ser Ser Gln Ser Leu Val His Ser Asn Gly Asp Thr Tyr Leu Asp
1               5                   10                  15

Trp Tyr Leu Gln Lys Pro Gly Gln Ser Pro Gln Leu Leu Ile Tyr Lys
                20                  25                  30
```

```
Val Ser Asn Arg Ala Ser Gly Val
         35                  40

<210> SEQ ID NO 39
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Lys Ser Ser Gln Ser Leu Val His Ser Asn Gly Asp Thr Tyr Leu Tyr
1               5                   10                  15

Trp Tyr Leu Gln Lys Pro Gly Gln Pro Pro Gln Leu Leu Ile Tyr Lys
            20                  25                  30

Val Ser Asn Arg Phe Ser Gly Val
         35                  40

<210> SEQ ID NO 40
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Arg Ser Ser Gln Ser Leu Val His Ser Asn Gly Asp Thr Tyr Phe His
1               5                   10                  15

Trp Tyr Leu Gln Lys Pro Gly Gln Ser Pro Gln Leu Leu Ile Tyr Lys
            20                  25                  30

Val Ser Asn Arg Phe Ser Gly Val
         35                  40

<210> SEQ ID NO 41
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Arg Ser Ser Gln Ser Leu Val His Ser Asn Gly Asp Thr Tyr Phe His
1               5                   10                  15

Trp Tyr Leu Gln Lys Pro Gly Gln Ser Pro Gln Leu Leu Ile Tyr Lys
            20                  25                  30

Val Ser Asn Arg Phe Ser Gly Val
         35                  40

<210> SEQ ID NO 42
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Arg Ser Ser Gln Ser Leu Val His Ser Asn Gly Asp Thr Tyr Phe His
1               5                   10                  15

Trp Tyr Leu Gln Lys Pro Gly Gln Ser Pro Gln Leu Leu Ile Tyr Lys
```

Val Ser Asn Arg Phe Ser Gly Val
            35                  40

<210> SEQ ID NO 43
<211> LENGTH: 40
<212> TYPE: PRT
<213> ORGANISM: Homo sapiens

<400> SEQUENCE: 43

Arg Ser Ser Gln Ser Leu Val Tyr Ser Asp Gly Asn Thr Tyr Leu Asn
1               5                   10                  15

Trp Phe Gln Gln Arg Pro Gly Gln Ser Pro Arg Leu Ile Tyr Lys
            20                  25                  30

Val Ser Asn Arg Asp Ser Gly Val
            35                  40

<210> SEQ ID NO 44
<211> LENGTH: 40
<212> TYPE: PRT
<213> ORGANISM: Homo sapiens

<400> SEQUENCE: 44

Arg Ser Ser Gln Ser Leu Leu His Ser Asn Gly Tyr Asn Tyr Leu Asp
1               5                   10                  15

Trp Tyr Leu Gln Lys Pro Gly Gln Ser Pro Gln Leu Leu Ile Tyr Leu
            20                  25                  30

Gly Ser Asn Arg Ala Ser Gly Val
            35                  40

<210> SEQ ID NO 45
<211> LENGTH: 40
<212> TYPE: PRT
<213> ORGANISM: Homo sapiens

<400> SEQUENCE: 45

Lys Ser Ser Gln Ser Leu Leu His Ser Asp Gly Lys Thr Tyr Leu Tyr
1               5                   10                  15

Trp Tyr Leu Gln Lys Pro Gly Gln Pro Pro Gln Leu Leu Ile Tyr Glu
            20                  25                  30

Val Ser Asn Arg Phe Ser Gly Val
            35                  40

<210> SEQ ID NO 46
<211> LENGTH: 40
<212> TYPE: PRT
<213> ORGANISM: Homo sapiens

<400> SEQUENCE: 46

Arg Ser Ser Gln Ser Leu Leu His Ser Asn Gly Tyr Asn Tyr Leu Asp
1               5                   10                  15

Trp Tyr Leu Gln Lys Pro Gly Gln Ser Pro Gln Leu Leu Ile Tyr Leu
            20                  25                  30

Gly Ser Asn Arg Ala Ser Gly Val
            35                  40

<210> SEQ ID NO 47
<211> LENGTH: 40
<212> TYPE: PRT
<213> ORGANISM: Homo sapiens

```
<400> SEQUENCE: 47

Lys Ser Ser Gln Ser Leu Leu His Ser Asp Gly Lys Thr Tyr Leu Tyr
1               5                   10                  15

Trp Tyr Leu Gln Lys Pro Gly Gln Pro Pro Gln Leu Leu Ile Tyr Glu
                20                  25                  30

Val Ser Asn Arg Phe Ser Gly Val
            35                  40

<210> SEQ ID NO 48
<211> LENGTH: 40
<212> TYPE: PRT
<213> ORGANISM: Homo sapiens

<400> SEQUENCE: 48

Arg Ser Ser Gln Ser Leu Val Tyr Ser Asp Gly Asn Thr Tyr Leu Asn
1               5                   10                  15

Trp Phe Gln Gln Arg Pro Gly Gln Ser Pro Arg Arg Leu Ile Tyr Lys
                20                  25                  30

Val Ser Asn Arg Asp Ser Gly Val
            35                  40

<210> SEQ ID NO 49
<211> LENGTH: 112
<212> TYPE: PRT
<213> ORGANISM: Mus musculus

<400> SEQUENCE: 49

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asp Thr Tyr Phe His Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Thr
                85                  90                  95

Thr His Ala Pro Phe Thr Phe Gly Ser Gly Thr Lys Leu Glu Ile Lys
            100                 105                 110

<210> SEQ ID NO 50
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(36)
<223> OTHER INFORMATION: Any amino acid
<220> FEATURE:
<221> NAME/KEY: MOD_RES
<222> LOCATION: (51)..(61)
<223> OTHER INFORMATION: Any amino acid

<400> SEQUENCE: 50

Gln Ile Gln Leu Gln Glu Ser Gly Pro Gly Leu Val Lys Pro Ser Gln
1               5                   10                  15
```

```
Ser Leu Ser Leu Thr Cys Ser Val Thr Gly Xaa Xaa Xaa Xaa Xaa
            20                  25                  30

Xaa Xaa Xaa Xaa Thr Trp Ile Arg Gln Phe Pro Gly Lys Lys Leu Glu
        35                  40                  45

Trp Met Xaa Xaa Xaa Xaa Xaa Xaa Xaa Xaa Xaa Xaa Asn Pro Ser
    50                  55                  60

Leu Lys Ser Arg Ile Ser Ile Thr Arg Asp Thr Ser Lys Asn Gln Phe
65                  70                  75                  80

Leu Leu His Leu Asn Ser Val Thr Thr Glu Asp Thr Ala Thr Tyr Tyr
                85                  90                  95

Cys Ala Arg

<210> SEQ ID NO 51
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(35)
<223> OTHER INFORMATION: Any amino acid
<220> FEATURE:
<221> NAME/KEY: MOD_RES
<222> LOCATION: (50)..(60)
<223> OTHER INFORMATION: Any amino acid

<400> SEQUENCE: 51

Ile Gln Leu Gln Glu Ser Gly Pro Gly Leu Val Lys Pro Ser Gln Ser
1               5                   10                  15

Leu Ser Leu Thr Cys Ser Val Thr Gly Xaa Xaa Xaa Xaa Xaa Xaa
            20                  25                  30

Xaa Xaa Xaa Thr Trp Ile Arg Gln Phe Pro Gly Lys Lys Leu Glu Trp
        35                  40                  45

Met Xaa Xaa Xaa Xaa Xaa Xaa Xaa Xaa Xaa Xaa Asn Pro Ser Leu
    50                  55                  60

Lys Ser Arg Ile Ser Ile Thr Arg Asp Thr Ser Lys Asn Gln Phe Leu
65                  70                  75                  80

Leu His Leu Asn Ser Val Thr Thr Glu Asp Thr Ala Thr Tyr Tyr Cys
                85                  90                  95

Ala Arg

<210> SEQ ID NO 52
<211> LENGTH: 97
<212> TYPE: PRT
<213> ORGANISM: Unknown
<220> FEATURE:
<223> OTHER INFORMATION: Description of Unknown:
      PDB-1 sequence

<400> SEQUENCE: 52

Val Gln Leu Gln Glu Ser Gly Pro Gly Leu Val Lys Pro Ser Gln Ser
1               5                   10                  15

Leu Ser Leu Thr Cys Thr Val Thr Gly Tyr Ser Ile Ser Ser Asp Tyr
            20                  25                  30

Ala Trp Asn Trp Ile Arg Gln Phe Pro Gly Asn Lys Leu Glu Trp Met
        35                  40                  45

Gly Tyr Ile Ser Tyr Ser Gly Ser Thr Ser Tyr Asn Pro Ser Leu Lys
    50                  55                  60
```

Ser Arg Ile Ser Ile Thr Arg Asp Thr Ser Lys Asn Gln Phe Phe Leu
65                  70                  75                  80

Gln Leu Ser Ser Val Thr Thr Glu Asp Thr Ala Thr Tyr Tyr Cys Ala
                85                  90                  95

Arg

<210> SEQ ID NO 53
<211> LENGTH: 14
<212> TYPE: PRT
<213> ORGANISM: Cricetulus migratorius

<400> SEQUENCE: 53

Thr Gly Phe Ser Ile Thr Thr Ser Gly Tyr Tyr Trp Thr Trp
1               5                   10

<210> SEQ ID NO 54
<211> LENGTH: 18
<212> TYPE: PRT
<213> ORGANISM: Cricetulus migratorius

<400> SEQUENCE: 54

Ser Val Thr Gly Phe Ser Ile Thr Thr Ser Gly Tyr Tyr Trp Thr Trp
1               5                   10                  15

Ile Arg

<210> SEQ ID NO 55
<211> LENGTH: 18
<212> TYPE: PRT
<213> ORGANISM: Unknown
<220> FEATURE:
<223> OTHER INFORMATION: Description of Unknown:
      Sbjct sequence

<400> SEQUENCE: 55

Thr Val Ser Gly Gly Ser Ile Ser Ser Gly Asp Tyr Tyr Trp Ser Trp
1               5                   10                  15

Ile Arg

<210> SEQ ID NO 56
<211> LENGTH: 15
<212> TYPE: PRT
<213> ORGANISM: Cricetulus migratorius

<400> SEQUENCE: 56

Trp Met Gly Tyr Ile Gly Tyr Asn Ser Lys Thr Tyr Tyr Asn Pro
1               5                   10                  15

<210> SEQ ID NO 57
<211> LENGTH: 18
<212> TYPE: PRT
<213> ORGANISM: Cricetulus migratorius

<400> SEQUENCE: 57

Tyr Cys Ala Arg Ser Leu Tyr Gly Gly Tyr Lys Asp Ala Phe Asp Ser
1               5                   10                  15

Trp Gly

<210> SEQ ID NO 58
<211> LENGTH: 18
<212> TYPE: PRT
<213> ORGANISM: Homo sapiens

<400> SEQUENCE: 58

```
Tyr Cys Ala Arg Asp Pro Tyr Gly Gly Gly Lys Ser Glu Phe Asp Tyr
1               5                   10                  15

Trp Gly

<210> SEQ ID NO 59
<211> LENGTH: 113
<212> TYPE: PRT
<213> ORGANISM: Unknown
<220> FEATURE:
<223> OTHER INFORMATION: Description of Unknown:
      2eksb sequence

<400> SEQUENCE: 59

Gln Val Gln Leu Gln Glu Ser Gly Pro Gly Leu Met Lys Pro Ser Glu
1               5                   10                  15

Thr Leu Ser Leu Thr Cys Ser Val Ser Gly Asp Ser Ile Arg Ser Asp
            20                  25                  30

Tyr Trp Ser Trp Ile Arg Gln Pro Pro Gly Lys Gly Leu Glu Trp Ile
        35                  40                  45

Gly Tyr Val Ser Tyr Ser Gly Ser Thr Tyr Tyr Asn Pro Ser Leu Lys
    50                  55                  60

Ser Arg Val Thr Ile Ser Val Asp Thr Ser Lys Asn Arg Phe Ser Leu
65                  70                  75                  80

Lys Leu Asn Ser Val Thr Ala Ala Asp Thr Ala Val Tyr Tyr Cys Ala
                85                  90                  95

Arg Trp Asp Gly Asp Tyr Trp Gly Gln Gly Ile Leu Val Thr Val Ser
            100                 105                 110

Ser

<210> SEQ ID NO 60
<211> LENGTH: 154
<212> TYPE: PRT
<213> ORGANISM: Unknown
<220> FEATURE:
<223> OTHER INFORMATION: Description of Unknown:
      32c2b sequence

<400> SEQUENCE: 60

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Ser Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Ser Ser Val Thr Thr Glu Asp Thr Ala Thr Tyr Tyr Cys
                85                  90                  95

Ala Arg Gly Tyr Tyr Gly Ser Ser His Ser Pro Val Trp Gly Ala Gly
            100                 105                 110

Thr Thr Val Thr Val Ser Ser Ala Lys Thr Thr Pro Pro Val Tyr
        115                 120                 125

Pro Leu Val Pro Gly Ser Leu Ala Gln Thr Asn Ser Met Val Thr Leu
    130                 135                 140

Gly Cys Leu Val Lys Gly Tyr Phe Pro Glu
```

```
145                 150

<210> SEQ ID NO 61
<211> LENGTH: 150
<212> TYPE: PRT
<213> ORGANISM: Unknown
<220> FEATURE:
<223> OTHER INFORMATION: Description of Unknown:
      3b2uf sequence

<400> SEQUENCE: 61

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asp Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Val Asn Ser Val Thr Ala Ala Asp Thr Ala Val Tyr Tyr
                85                  90                  95

Cys Ala Arg Val Ser Ile Phe Gly Val Gly Thr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Gly Thr Ala Ala Leu Gly Cys Leu Val
    130                 135                 140

Lys Asp Tyr Phe Pro Glu
145                 150

<210> SEQ ID NO 62
<211> LENGTH: 157
<212> TYPE: PRT
<213> ORGANISM: Homo sapiens

<400> SEQUENCE: 62

Gln Val Lys Leu Leu Glu Gln Ser Gly Ala Glu Val Lys Lys Pro Gly
1               5                   10                  15

Ala Ser Val Lys Val Ser Cys Lys Ala Ser Gly Tyr Ser Phe Thr Ser
            20                  25                  30

Tyr Gly Leu His Trp Val Arg Gln Ala Pro Gly Gln Arg Leu Glu Trp
        35                  40                  45

Met Gly Trp Ile Ser Ala Gly Thr Gly Asn Thr Lys Tyr Ser Gln Lys
    50                  55                  60

Phe Arg Gly Arg Val Thr Phe Thr Arg Asp Thr Ser Ala Thr Thr Ala
65                  70                  75                  80

Tyr Met Gly Leu Ser Ser Leu Arg Pro Glu Asp Thr Ala Val Tyr Tyr
                85                  90                  95

Cys Ala Arg Asp Pro Tyr Gly Gly Lys Ser Glu Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu
```

-continued

```
145                 150                 155
```

<210> SEQ ID NO 63
<211> LENGTH: 18
<212> TYPE: PRT
<213> ORGANISM: Mus musculus

<400> SEQUENCE: 63

```
Asp Gly Ser Thr Thr Tyr Asn Ser Ala Leu Lys Ser Arg Leu Ser Ile
1               5                   10                  15

Ser Lys
```

<210> SEQ ID NO 64
<211> LENGTH: 19
<212> TYPE: PRT
<213> ORGANISM: Mus musculus

<400> SEQUENCE: 64

```
Thr Val Ser Gly Phe Ser Leu Asp Ser Tyr Gly Val His Trp Val Arg
1               5                   10                  15

Gln Pro Pro
```

<210> SEQ ID NO 65
<211> LENGTH: 18
<212> TYPE: PRT
<213> ORGANISM: Mus musculus

<400> SEQUENCE: 65

```
Asp Gly Thr Thr Thr Tyr Asn Ser Ala Leu Lys Ser Arg Leu Ser Ile
1               5                   10                  15

Thr Lys
```

<210> SEQ ID NO 66
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Asp Gly Thr Thr Tyr Tyr Ala Asp Ser Val Lys Gly Arg Phe Thr Ile
1               5                   10                  15

Ser Arg
```

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Asp Gly Thr Lys Tyr Tyr Ala Asp Ser Val Lys Gly Arg Phe Thr Ile
1               5                   10                  15

Ser Arg
```

<210> SEQ ID NO 68
<211> LENGTH: 18
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 68

Asp Gly Thr Thr Asn Tyr Asn Pro Ser Leu Lys Ser Arg Val Thr Ile
1               5                   10                  15

Ser Val

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Gly Thr Thr Thr Tyr Asn Ser Ala Leu Lys Ser Arg Phe Thr Ile
1               5                   10                  15

Ser Arg

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Thr Asn Lys Tyr Tyr Ala Asp Ser Val Lys Gly Arg Phe Thr Ile
1               5                   10                  15

Ser Arg

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Gly Thr Thr Thr Tyr Pro Gly Ser Val Lys Gly Arg Phe Thr Ile
1               5                   10                  15

Ser Arg

<210> SEQ ID NO 72
<211> LENGTH: 24
<212> TYPE: PRT
<213> ORGANISM: Cricetulus migratorius

<400> SEQUENCE: 72

Gln Ile Gln Leu Gln Glu Ser Gly Pro Gly Leu Val Lys Pro Ser Gln
1               5                   10                  15

Ser Leu Ser Leu Thr Cys Ser Val
                20

<210> SEQ ID NO 73
<211> LENGTH: 18
<212> TYPE: PRT
<213> ORGANISM: Homo sapiens

<400> SEQUENCE: 73
```

Gly Ser Asn Lys Tyr Tyr Ala Asp Ser Val Lys Gly Arg Phe Thr Ile
1               5                   10                  15

Ser Arg

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asp Gly Thr Thr Thr Tyr Asn Ser Ala Leu Lys Ser Arg Leu Thr Ile
1               5                   10                  15

Ser Arg

<210> SEQ ID NO 75
<211> LENGTH: 18
<212> TYPE: PRT
<213> ORGANISM: Homo sapiens

<400> SEQUENCE: 75

Gly Gly Ser Thr Tyr Tyr Ala Asp Ser Val Lys Gly Arg Phe Thr Ile
1               5                   10                  15

Ser Arg

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Gly Thr Thr Asn Tyr Asn Pro Ala Leu Lys Ser Arg Val Thr Ile
1               5                   10                  15

Ser Val

<210> SEQ ID NO 77
<211> LENGTH: 18
<212> TYPE: PRT
<213> ORGANISM: Homo sapiens

<400> SEQUENCE: 77

Ser Gly Ser Thr Asn Tyr Asn Pro Ser Leu Lys Ser Arg Val Thr Ile
1               5                   10                  15

Ser Val

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Gly Thr Lys Ser Tyr Ser Thr Ser Leu Lys Ser Arg Leu Thr Ile
1               5                   10                  15

Ser Lys

```
<210> SEQ ID NO 79
<211> LENGTH: 18
<212> TYPE: PRT
<213> ORGANISM: Homo sapiens

<400> SEQUENCE: 79

Asn Asp Glu Lys Ser Tyr Ser Thr Ser Leu Lys Ser Arg Leu Thr Ile
1               5                   10                  15

Ser Lys

<210> SEQ ID NO 80
<211> LENGTH: 18
<212> TYPE: PRT
<213> ORGANISM: Homo sapiens

<400> SEQUENCE: 80

Ala Gly Asp Thr Tyr Tyr Pro Gly Ser Val Lys Gly Arg Phe Thr Ile
1               5                   10                  15

Ser Arg

<210> SEQ ID NO 81
<211> LENGTH: 40
<212> TYPE: PRT
<213> ORGANISM: Mus musculus

<400> SEQUENCE: 81

Arg Ser Ser Gln Ser Leu Val His Ser Asn Gly Asn Thr Tyr Leu His
1               5                   10                  15

Trp Tyr Leu Gln Lys Pro Gly Gln Ser Pro Lys Leu Leu Ile Tyr Lys
            20                  25                  30

Val Ser Asn Arg Phe Ser Gly Val
            35                  40

<210> SEQ ID NO 82
<211> LENGTH: 40
<212> TYPE: PRT
<213> ORGANISM: Mus musculus

<400> SEQUENCE: 82

Arg Ser Ser Gln Ser Leu Val His Ser Asn Gly Asp Thr Tyr Phe His
1               5                   10                  15

Trp Tyr Leu Gln Lys Pro Gly Gln Ser Pro Lys Leu Leu Ile Tyr Lys
            20                  25                  30

Val Ser Asn Arg Phe Ser Gly Val
            35                  40
```

THREE-DIMENSIONAL STRUCTURE-BASED HUMANIZATION METHOD

CROSS-REFERENCE TO RELATED APPLICATIONS

This application is a National Stage Application of PCT/EP2018/070372 filed Jul. 27, 2018, which claims priority from European Patent Application No. 17183933.5, filed on Jul. 31, 2017. The priority of both said PCT and European Patent Application are claimed. Each of prior mentioned applications is hereby incorporated by reference herein in its entirety.

SEQUENCE LISTING

The instant application contains a Sequence Listing which has been submitted electronically in ASCII format and is hereby incorporated by reference in its entirety. Said ASCII copy, created on Dec. 22, 2022, is named 036844-102271_(P34329)_SL.txt and is 33,842 bytes in size.

Herein is reported a method for the humanization of non-human antibodies using a structure-based approach. With the herein reported method it is possible to determine (the requirement for and) the suitability of specific (back- or forward-)mutations of amino acid residues at defined positions of a selected human or humanized acceptor sequence. The topology, the three-dimensional structure and the interactions of the respective residue as well as its change are considered. Thereby the influence on antigen binding of a specific amino acid residue change is addressed.

BACKGROUND

The interaction of an antibody with its antigen is based on its 3-dimensional structure. The antibody paratope is formed by the 6 CDR (complementarity determining region) loops, recognizing a complementary epitope on the antigen's surface. In case of antibodies specific for a small antigen (such as small molecules) only a few amino acids from some CDRs, but not all are involved in the antigen recognition. Generally, VH (variable antibody heavy chain domain) CDRs (in particular, VH CDR3) have a higher contribution to formation of contacts with antigens, comparing to VL (variable antibody light chain domain) CDRs, and the geometric center of the antigen-antibody contact lies closely to VH CDR3. CDR amino acid residues involved in direct antigen contacts are called specificity determining regions (SDRs). By analysis of 3-dimensional structure of the antigen-antibody complex amino acid residues directly contacting the antigen can be identified based on their distance. FR (framework) residues spaced between the CDRs can also participate in antigen recognition, but to a lesser extent (the surface of such regions may account for up to 15% of the antigen and antibody contact surface) (see, e.g., Altshuler, E. P., Chemie 50 (2010) 203-258; Bujotzek, A., et al., mAbs 8 (2016) 288-305).

The secondary and tertiary antibody structure is disclosed, e.g., in EP 0 239 400. The four framework regions largely adopt a β-sheet conformation and the CDRs form loops connecting, and in some cases forming part of the β-sheet structure. The CDRs are held in close proximity by the framework regions and, with the CDRs from the other variable domain, contribute to the formation of the antigen binding site (see, e.g., Poljak, R. J., et al., Proc. Natl. Acad. Sci. USA, 70 (1973) 3305-3310; Segal, D. M., et al., Proc. Natl. Acad. Sci. USA, 71(1974) 4298-4302, Marquart, M., et al., J. Mol. Biol., 141, (1980) 369-391).

Not all residues within a variable domain are solvent accessible (see, e.g., Amit, A. G., et al., Science, 233 (1986) 747-753).

Within a domain, the packing together and orientation of the two disulphide bonded β-sheets (and therefore the ends of the CDR loops) are relatively conserved, although, small shifts in packing and orientation of these β-sheets do occur (see, e.g., Lesk, A. M. and Chothia, C., J. Mol. Biol., 160, 325-342, 1982; Chothia, C., et al., J. Mol. Biol., 186 (1985) 651-653, 1985).

The variable regions of the two parts of an antigen binding site are held in the correct orientation by inter-chain non-covalent interactions. These may involve amino-acid residues within the CDRs.

Thus, in order to transfer the antigen binding capacity of one variable domain to another, it may not be necessary to replace all of the CDRs with the complete CDRs from the donor variable region. It may only be required to transfer those residues, which are accessible from the antigen binding site—CDR residues as well as framework residues. It may also be necessary to ensure that residues essential for inter-chain interactions are preserved in the acceptor variable domain.

The function of an immunoglobulin molecule is dependent on its three dimensional structure, which in turn is dependent on its primary amino acid sequence.

Modeling the Fv region of antibodies is disclosed by Bujotzek et al. (MAbs. 7 (2015) 838-852). WO 2005/061540 discloses a method for the humanization of antibodies and humanized antibodies obtained thereby. Humanizing antibodies by CDR grafting is disclosed by Williams et al. (in "Antibody Engineering", Springer (Berlin), 2010, pages 319-339). WO 2014/100542 discloses high-throughput antibody humanization. Prediction of VH-VL domain orientation for antibody variable domain modeling is disclosed by Bujotzek et al. (Prot. Struct. Funct. Bioinf. 83 (2015) 681-695). WO 2016/062734 discloses VH-VL-interdomain angle based antibody humanization.

SUMMARY

Herein is reported a method for the humanization of non-human antibodies using a structure-based approach. With the method according to the invention it is possible to identify (the requirement for) specific (back)mutation of amino acid residues at defined positions of a selected human or humanized acceptor sequence, which had been selected as acceptor for the non-human antibody's CDRs or individual residues thereof. This primary selection is done as known from the art. The identification of residues to be backmutated takes into account the topology, the three-dimensional structure and the interactions of the respective residue and the effect of a change.

Thereby an improved prediction of the influence on antigen binding of a specific amino acid residue change can be made and also quantified.

It has been found that the humanized antibodies obtained with a method according to the invention have more humaneness (human character) compared to humanized antibodies obtained with conventional humanization methods not using an additional topological characterization.

The method according to the current invention comprises as essential step the quantification of the effect on topology, i.e. three dimensional structure and orientation, of each amino acid difference between the selected acceptor sequence for the transfer of the complementarity determining regions (CDRs) of the non-human antibody and the parental non-human antibody.

In one embodiment the (topological) quantification is done by providing a score for each change/difference individually or for all changes/differences together. This score is based on the one hand on the structural difference between the changed amino acid residues and on the other hand on the topology of the position of said change. The score is in one embodiment assigned base on/using a three-dimensional homology model. The score reflects the impact of the amino acid difference on the framework stability or CDR conformation and is as follows: 0: no influence; 1: slight influence; 2: moderate influence; 3: may affect framework stability; 4: will break framework stability or CDR conformation.

By assigning for each amino acid residue difference at a respective position present in any human germline sequence an individual score a full matrix of possible changes is obtained.

The invention is based at least in part on the finding that by a quantitative analysis of the three-dimensional structure of an antibody, more precisely of the structural difference between the parent non-human antibody structure and the structure of the humanization candidate, suitable (and required) amino acid change(s) can be identified, which result(s) in a different, preferably lower or even none, influence on/deformation of the framework/CDR conformation and thereby, amongst other things, an increased binding of the humanized antibody to its antigen. Thus, the current invention provides for an improved humanization method.

One aspect of the invention is a method for providing (or synthesizing or identifying or producing) a nucleic acid sequence encoding an (humanized) immunoglobulin variable domain comprising the following steps
  a) aligning the amino acid sequence of a non-human heavy chain or light chain variable domain
    with
    a first humanized variant of said non-human heavy chain or light chain variable domain obtained by grafting the CDRs or hypervariable regions or specificity determining residues of the respective non-human antibody heavy chain or light chain variable domain on
      i) a human germline amino acid sequence with the highest sequence homology to the non-human variable domain,
      or
      ii) two or more human germline amino acid sequence fragments that when aligned form a complete variable domain and have a homology higher than a single human germline amino acid sequence,
      or
      iii) a human germline amino acid sequence that allows maintaining VH/VL angle,
      or
      iv) a humanized antibody variable domain,
      (with maximal level of amino acid sequence identity),
  b) identifying (aligned) framework positions, in which the non-human heavy chain or light chain variable domain and the first humanized variant of said non-human heavy chain or light chain variable domain have different amino acid residues, which, due to the difference, influence antigen binding and/or three dimensional structure of the variable domain (in combination with the respective other variable domain as Fv),
  c) modifying the first humanized variant of said non-human heavy chain or light chain variable domain by replacing one or more amino acid residue identified in step b) with an amino acid residue that influences antigen binding and/or the three dimensional structure of the variable domain (in combination with the respective other variable domain as Fv) less than the replaced amino acid residue,
  d) synthesizing a nucleic acid sequence encoding the modified variable domain and thereby providing (or synthesizing or identifying) a nucleic acid sequence encoding an immunoglobulin variable domain.

In one embodiment step b) further comprises generating a three-dimensional model of the non-human variable domains or the non-human antibody using homology modeling.

In one embodiment step b) further comprises assigning to the respective positions one of the topology classifiers I, E, C, A, L, S, or N.

In one embodiment step b) further comprises assigning a score to each difference of 0, 1, 2, 3, or 4.

In one embodiment in step b) further comprises assigning a score of 0, 1, 2, 3, or 4 to each difference whereby
  a score of 0 is assigned to a change of an amino acid residue with the topology E to any amino acid residue except proline,
  a change to proline is assigned a score of 3 or 4 if the proline replacement changes the phi and psi angles around this residue, if a change to proline is not changing the conformation of the amino acid stretch around the residue it is assigned a score of 0 or 1,
  a score of 0 is assigned to a change of an amino acid residue with the topology I to an amino acid residue with a smaller side chain, the replacement with an amino acid residue with a side chain that has one carbon atom more will be assigned a score of 1, the replacement with an amino acid residue with a side chain that has two carbon atoms more will be assigned a score of 2, the replacement with an amino acid residue with a side chain that has three carbon atoms more will be assigned a score of 3, and all other changes will be assigned a score of 4,
  a score of 4 is assigned to a change of an amino acid residue with the topology A to any amino acid residue,
  a score of 3 or 4 is assigned to the change of an amino acid residue with the topology C to a non-hydrophobic amino acid residue,
  a score of 3 is assigned to a change of an amino acid residue with the topology S to an oppositely charged or not-charged amino acid residue if the salt bridge is solvent exposed and a score of 4 is assigned if the salt bridge is internal.

DETAILED DESCRIPTION

The antigen binding site of an antibody is formed by the heavy chain variable domain (VH) and the light chain variable domain (VL). These domains interact via the five-stranded beta-sheets to form a nine-stranded beta-barrel of about 8.4 Å radius, with the strands at the domain interface inclined at approximately 50° to one another. Thereby the HVRs, i.e. the amino acid loops formed by the HVR amino acid residues are brought in close proximity to each other. This can be seen when viewed from the top of the structure. Also the HVR contribute to 25% or more of the VH/VL interface.

For the determination of the CDRs/HVRs different methods have been reported in the art. The most commonly used method is the definition according to Kabat, which is based on antibody amino acid sequence variability (see e.g. Sequences of Proteins of immunological Interest, US Department of Health and Human Services (1991)). Another definition has been reported by Chothia (see, e.g., Chothia, C., et al. J. Mol. Biol. 227 (1992) 799-817; Tomlinson, I. M., et al., EMBO J. 14 (1995) 4628-4638), which takes into account the antigen binding site in order to define hypervariable loops. The revised Chothia numbering approach is based on the Chothia numbering scheme and includes also the framework residues with positional corrected FR indels (see, e.g., Abhinandan, K. R. and Martin, A. C., Mol. Immunol. 45 (2008) 3832-3839). A further method is the AbM definition used by Oxford Molecular's AbM antibody modeling software (see, e.g., Protein Sequence and Structure Analysis of Antibody Variable Domains. In: Antibody Engineering Lab Manual (Ed.: Duebel, S. and Kontermann, R., Springer-Verlag, Heidelberg)). Another method is called Enhanced Chothia Numbering (proposed by Martin, A.C.R.; see, e.g., www.bioinfo.org.uk/index.html, specifically www.bioinf.org.uk/abs/). Another method is based on the analysis of antibody-antigen complex crystal structures to determine "contact" HVRs (MacCallum, R. M., et al., J. Mol. Biol. 262 (1996) 732-745). A novel or extended canonical alignment was suggested by North, B., et al. (J. Mol. Biol. 406 (2011) 228-256). Unlike Chothia's analysis, they have found it most intuitive to group CDRs into CDR type (L1, L2, etc.) and loop length. When referred to these as "CDR-length combinations" or simply "CDR-lengths" for short. They have defined the CDRs differently from the most commonly used Kabat and Chothia schemes. The methods as reported herein can be practiced with any of these methods.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs include
(a) hypervariable loops occurring at amino acid residues 26-32 (L1), 50-52 (L2), 91-96 (L3), 26-32 (H1), 53-55 (H2), and 96-101 (13) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242.);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

Therefore, aspects and embodiments reported herein using the Kabat CDR/HVR definition can likewise be implemented using one of the other CDR/HVR determination methods. The following Table provides a comparison of the HVR residues determined with the different methods.

|  | Kabat | Chothia | AbM | contact |
|---|---|---|---|---|
| HVR-L1 | 24-34 | 26-32 | 24-34 | 30-36 |
| HVR-L2 | 50-56 | 50-52 | 50-56 | 46-55 |
| HVR-L3 | 89-97 | 91-96 | 89-97 | 89-96 |
| HVR-H1 (according to Kabat) | 31-35B | 26-32 | 26-35B | 30-35B |
| HVR-H1 (according to Chothia) | 31-35 | 26-32 | 26-35 | 30-35B |
| HVR-H2 | 50-65 | 53-55 | 50-58 | 47-58 |
| HVR-H3 | 95-102 | 96-101 | 95-102 | 93-101 |

Beside the different CDR definitions also different methods for numbering the variable domain amino acid residues are available. Kabat and co-authors (Wu, T. I. and Kabat, E. A., J. Exp. Med. 132 (1970) 211-250; Kabat, E. A., et al., Sequence of Proteins of Immunological Interest. Bethesda: National Institute of Health (1983)) used a numbering based on sequence alignment and homology. Chothia and Lesk (Chothia, C. and Lesk, A. M., J. Mol. Biol. 196 (1987) 901-917; Chothia, C., et al., Nature, 342 (1989) 877-883) used a numbering based on a structural alignment. Lefranc and colleagues (Giudicelli, V. et al., Nucl. Acids Res. 25 (1997) 206-211; Lefranc, M. P., et al., Dev. Comp. Immunol. 27 (2003) 55-77) developed the IMGT numbering scheme. The AHo numbering scheme (Honegger, A. and Plueckthun, A., J. Mol. Biol. 309 (2001) 657-670) is based on spatially aligned 3D structures.

The WolfGuy numbering defines CDR regions as the set union of the Kabat and Chothia definition. Furthermore, the numbering scheme annotates CDR loop tips based on CDR length (and partly based on sequence) so that the index of a CDR position indicates if a CDR residue is part of the ascending or the descending loop. A comparison with established numbering schemes is shown in the following Tables.

TABLE

Numbering of CDR-L3 and CDR-H3 using Chothia/Kabat (Ch-Kb), Honegger and WolfGuy numbering schemes. The latter has increasing numbers from the N-terminal basis to the CDR peak and decreasing ones starting from the C-terminal CDR end. Rabat schemes fix the two last CDR residues and introduce letters to accommodate for the CDR length. In contrast to Rabat nomenclature, the Honegger numbering does not use letters and is common for VH and VL.

| WolfGuy VL | Ch-Kb VL | Honegger | Ch-Kb VH | WolfGuy VH |
|---|---|---|---|---|
| 730 | 84 | 102 | 88 | 326 |
| 731 | 85 | 103 | 89 | 327 |
| 732 | 86 | 104 | 90 | 328 |
| 733 | 87 | 105 | 91 | 329 |
| 734 | 88 | C | 92 | 330 |
| 751 | 89 | 107 | 93 | 331 |
| 752 | 90 | 108 | 94 | 332 |
| 753 | 91 | 109 | 95 | 351 |
| 754 | 92 | 110 | 96 | 352 |
| 755 | 93 | 111 | 97 | 353 |
| 756 | 94 | 112 | 98 | 354 |
| 757 | 95 | 113 | 99 | 355 |
| 758 | 95a | 114 | 100 | 356 |
| 759 | 95b | 115 | 100a | 357 |
| 760 | 95c | 116 | 100b | 358 |
| 761 | 95d | 117 | 100c | 359 |
| 762 | 95e | 118 | 100d | 360 |
| 763 | 95f | 119 | 100e | 361 |
| 764 |  | 120 | 100f | 362 |
| 765 |  | 121 | 100g | 363 |

TABLE-continued

Numbering of CDR-L3 and CDR-H3 using Chothia/Kabat (Ch-Kb), Honegger and WolfGuy numbering schemes. The latter has increasing numbers from the N-terminal basis to the CDR peak and decreasing ones starting from the C-terminal CDR end. Rabat schemes fix the two last CDR residues and introduce letters to accommodate for the CDR length. In contrast to Rabat nomenclature, the Honegger numbering does not use letters and is common for VH and VL.

| WolfGuy VL | Ch-Kb VL | Honegger | Ch-Kb VH | WolfGuy VH |
|---|---|---|---|---|
| 766 | 122 | 100h | | 364 |
| 784 | 123 | 100i | | 384 |
| 785 | 124 | 100j | | 385 |
| 786 | 125 | 100k | | 386 |
| 787 | 126 | 100l | | 387 |
| 788 | 127 | | | 388 |
| 789 | 128 | | | 389 |
| 790 | 129 | | | 390 |
| 791 | 130 | | | 391 |
| 792 | 131 | | | 392 |
| 793 | 132 | | | 393 |
| 794 | | 133 | | 394 |
| 795 | | 134 | | 395 |
| 796 | | 135 | | 396 |
| 797 | | 136 | | 397 |
| 798 | 96 | 137 | 101 | 398 |
| 799 | 97 | 138 | 102 | 399 |
| 801 | 98 | F W | 103 | 401 |
| 802 | 99 | 140 | 104 | 402 |
| 803 | 100 | 141 | 105 | 403 |
| 804 | 101 | 142 | 106 | 404 |

TABLE

VH (left) and VL (right) sequence numbered with WolfGuy, Kabat and Chothia.

| | WolfGuy | Kabat | Chothia | | WolfGuy | Kabat | Chothia |
|---|---|---|---|---|---|---|---|
| VH-Framework 1 | 101 | 1 | 1 | VL-Framework 1 | 501 | 1 | 1 |
| | 102 | 2 | 2 | | 502 | 2 | 2 |
| | 103 | 3 | 3 | | 503 | 3 | 3 |
| | 104 | 4 | 4 | | 504 | 4 | 4 |
| | 105 | 5 | 5 | | 505 | 5 | 5 |
| | 106 | 6 | 6 | | 506 | 6 | 6 |
| | 107 | 7 | 7 | | 507 | 7 | 7 |
| | 108 | 8 | 8 | | 508 | 8 | 8 |
| | 109 | 9 | 9 | | 509 | 9 | 9 |
| | 110 | 10 | 10 | | 510 | 10 | 10 |
| | 111 | 11 | 11 | | 511 | 11 | 11 |
| | 112 | 12 | 12 | | 512 | 12 | 12 |
| | 113 | 13 | 13 | | 513 | 13 | 13 |
| | 114 | 14 | 14 | | 514 | 14 | 14 |
| | 115 | 15 | 15 | | 515 | 15 | 15 |
| | 116 | 16 | 16 | | 516 | 16 | 16 |
| | 117 | 17 | 17 | | 517 | 17 | 17 |
| | 118 | 18 | 18 | | 518 | 18 | 18 |
| | 119 | 19 | 19 | | 519 | 19 | 19 |
| | 120 | 20 | 20 | | 520 | 20 | 20 |
| | 121 | 21 | 21 | | 521 | 21 | 21 |
| | 122 | 22 | 22 | | 522 | 22 | 22 |
| | 123 | 23 | 23 | | 523 | 23 | 23 |
| | 124 | 24 | 24 | CDR-L1 | 551 | 24 | 24 |
| | 125 | 25 | 25 | | 552 | 25 | 25 |
| CDR-H1 | 151 | 26 | 26 | | 553 | 26 | 26 |
| | 152 | 27 | 27 | | 556 | 27 | 27 |
| | 153 | 28 | 28 | | 561 | 27a | 28 |
| | 154 | 29 | 29 | | 562 | 27b | 29 |
| | 155 | 30 | 30 | | 563 | 27c | 30 |
| | 156 | 31 | 31 | | 581 | 27d | 30a |
| | 157 | 32 | 31a | | 582 | 27e | 30b |
| | 158 | 33 | 31b | | 583 | 28 | 30c |
| | 193 | 34 | 31c | | 594 | 29 | 30d |
| | 194 | 35 | 31d | | 595 | 30 | 30e |
| | 195 | 35a | 31e | | 596 | 31 | 31 |
| | 196 | 35b | 32 | | 597 | 32 | 32 |
| | 197 | 35c | 33 | | 598 | 33 | 33 |
| | 198 | 35d | 34 | | 599 | 34 | 34 |
| | 199 | 35e | 35 | VL-Framework 2 | 601 | 35 | 35 |
| VH-Framework 2 | 201 | 36 | 36 | | 602 | 36 | 36 |
| | 202 | 37 | 37 | | 603 | 37 | 37 |
| | 203 | 38 | 38 | | 604 | 38 | 38 |
| | 204 | 39 | 39 | | 605 | 39 | 39 |
| | 205 | 40 | 40 | | 606 | 40 | 40 |
| | 206 | 41 | 41 | | 607 | 41 | 41 |
| | 207 | 42 | 42 | | 608 | 42 | 42 |
| | 208 | 43 | 43 | | 609 | 43 | 43 |

TABLE-continued

VH (left) and VL (right) sequence numbered with WolfGuy, Kabat and Chothia.

|  | WolfGuy | Kabat | Chothia |  | WolfGuy | Kabat | Chothia |
|---|---|---|---|---|---|---|---|
|  | 209 | 44 | 44 |  | 610 | 44 | 44 |
|  | 210 | 45 | 45 |  | 611 | 45 | 45 |
|  | 211 | 46 | 46 |  | 612 | 46 | 46 |
|  | 212 | 47 | 47 |  | 613 | 47 | 47 |
|  | 213 | 48 | 48 |  | 614 | 48 | 48 |
|  | 214 | 49 | 49 |  | 615 | 49 | 49 |
| CDR-H2 | 251 | 50 | 50 | CDR-L2 | 651 | 50 | 50 |
|  | 252 | 51 | 51 |  | 652 | * | * |
|  | 253 | 52 | 52 |  | 653 | * | * |
|  | 254 | 52a | 52a |  | 692 | * | * |
|  | 255 | 52b | 52b |  | 693 | * | * |
|  | 256 | 52c | 52c |  | 694 | 51 | 51 |
|  | 286 | 52d | 52d |  | 695 | 52 | 52 |
|  | 287 | 53 | 53 |  | 696 | 53 | 53 |
|  | 288 | 54 | 54 |  | 697 | 54 | 54 |
|  | 289 | 55 | 55 |  | 698 | 55 | 55 |
|  | 290 | 56 | 56 |  | 699 | 56 | 56 |
|  | 291 | 57 | 57 | VL-Framework 3 | 701 | 57 | 57 |
|  | 292 | 58 | 58 |  | 702 | 58 | 58 |
|  | 293 | 59 | 59 |  | 703 | 59 | 59 |
|  | 294 | 60 | 60 |  | 704 | 60 | 60 |
|  | 295 | 61 | 61 |  | 705 | 61 | 61 |
|  | 296 | 62 | 62 |  | 706 | 62 | 62 |
|  | 297 | 63 | 63 |  | 707 | 63 | 63 |
|  | 298 | 64 | 64 |  | 708 | 64 | 64 |
|  | 299 | 65 | 65 |  | 709 | 65 | 65 |
| VH-Framework 3 | 301 | 66 | 66 |  | 710 | 66 | 66 |
|  | 302 | 67 | 67 |  | 711 | 67 | 67 |
|  | 303 | 68 | 68 |  | 712 | 68 | 68 |
|  | 304 | 69 | 69 |  | 713 | * | * |
|  | 305 | 70 | 70 |  | 714 | * | * |
|  | 306 | 71 | 71 |  | 715 | 69 | 69 |
|  | 307 | 72 | 72 |  | 716 | 70 | 70 |
|  | 308 | 73 | 73 |  | 717 | 71 | 71 |
|  | 309 | 74 | 74 |  | 718 | 72 | 72 |
|  | 310 | 75 | 75 |  | 719 | 73 | 73 |
|  | 311 | 76 | 76 |  | 720 | 74 | 74 |
|  | 312 | 77 | 77 |  | 721 | 75 | 75 |
|  | 313 | 78 | 78 |  | 722 | 76 | 76 |
|  | 314 | 79 | 79 |  | 723 | 77 | 77 |
|  | 315 | 80 | 80 |  | 724 | 78 | 78 |
|  | 316 | 81 | 81 |  | 725 | 79 | 79 |
|  | 317 | 82 | 82 |  | 726 | 80 | 80 |
|  | 318 | 82a | 82a |  | 727 | 81 | 81 |
|  | 319 | 82b | 82b |  | 728 | 82 | 82 |
|  | 320 | 82c | 82c |  | 729 | 83 | 83 |
|  | 321 | 83 | 83 |  | 730 | 84 | 84 |
|  | 322 | 84 | 84 |  | 731 | 85 | 85 |
|  | 323 | 85 | 85 |  | 732 | 86 | 86 |
|  | 324 | 86 | 86 |  | 733 | 87 | 87 |
|  | 325 | 87 | 87 |  | 734 | 88 | 88 |
|  | 326 | 88 | 88 | CDR-L3 | 751 | 89 | 89 |
|  | 327 | 89 | 89 |  | 752 | 90 | 90 |
|  | 328 | 90 | 90 |  | 753 | 91 | 91 |
|  | 329 | 91 | 91 |  | 754 | 92 | 92 |
|  | 330 | 92 | 92 |  | 755 | 93 | 93 |
|  | 331 | 93 | 93 |  | 756 | 94 | 94 |
|  | 332 | 94 | 94 |  | 757 | 95 | 95 |
| CDR-H3 | 351 | 95 | 95 |  | 758 | 95a | 95a |
|  | 352 | 96 | 96 |  | 793 | 95b | 95b |
|  | 353 | 97 | 97 |  | 794 | 95c | 95c |
|  | 354 | 98 | 98 |  | 795 | 95d | 95d |
|  | 355 | 99 | 99 |  | 796 | 95e | 95e |
|  | 356 | 100 | 100 |  | 797 | 95f | 95f |
|  | 357 | 100a | 100a |  | 798 | 96 | 96 |
|  | 358 | 100b | 100b |  | 799 | 97 | 97 |
|  | 359 | 100c | 100c | VL-Framework 4 | 801 | 98 | 98 |
|  | 360 | 100d | 100d |  | 802 | 99 | 99 |
|  | 361 | 100e | 100e |  | 803 | 100 | 100 |
|  | 362 | 100f | 100f |  | 804 | 101 | 101 |
|  | 363 | 100g | 100g |  | 805 | 102 | 102 |
|  | 364 | 100h | 100h |  | 806 | 103 | 103 |
|  | 365 | 100i | 100i |  | 807 | 104 | 104 |
|  | 385 | 100j | * |  | 808 | 105 | 105 |
|  | 386 | 100k | * |  | 809 | 106 | 106 |
|  | 387 | 100l | * |  | 810 | 107/106A | 107 |

TABLE-continued

VH (left) and VL (right) sequence numbered with WolfGuy, Kabat and Chothia.

| | WolfGuy | Kabat | Chothia | WolfGuy | Kabat | Chothia |
|---|---|---|---|---|---|---|
| | 388 | 100m | * | | | |
| | 389 | 100n | * | | | |
| | 390 | 100o | * | | | |
| | 391 | 100p | * | | | |
| | 392 | 100q | * | | | |
| | 393 | 100r | * | | | |
| | 394 | 100s | * | | | |
| | 395 | 100t | * | | | |
| | 396 | 100u | * | | | |
| | 397 | 100v | * | | | |
| | 398 | 101 | 101 | | | |
| | 399 | 102 | 102 | | | |
| VH-Framework 4 | 401 | 103 | 103 | | | |
| | 402 | 104 | 104 | | | |
| | 403 | 105 | 105 | | | |
| | 404 | 106 | 106 | | | |
| | 405 | 107 | 107 | | | |
| | 406 | 108 | 108 | | | |
| | 407 | 109 | 109 | | | |
| | 408 | 110 | 110 | | | |
| | 409 | 111 | 111 | | | |
| | 410 | 112 | 112 | | | |
| | 411 | 113 | 113 | | | |

WolfGuy is designed such that structurally equivalent residues (i.e. residues that are very similar in terms of conserved spatial localization in the Fv structure) are numbered with equivalent indices (as far as possible).

Humanization Methods

General methods for antibody humanization are described, for example, in/by WO 92/22653; Bajorath, et al., J. Biol. Chem. 270 (1995) 22081-22084; Iba, Y., et al., Prot. Eng. 11 (1998) 361-370; WO 2002/84277; Luo et al., J. Immunol. Meth. 275 (2003) 31-40; WO 2004/006955; US 2004/0133357; Yazaki et al., Prot. Eng. Des. Sel. 17 (2004) 481-489; WO 2005/061540; WO 2006/096653; US 2006/0258852; WO 2007/109742; Leem, J., et al., mAbs 8 (2016) 1259-1268; U.S. Pat. Nos. 5,861,155, 6,479,284, US 2000/0660169, U.S. Pat. No. 6,407,213, US 1993/0146206, U.S. Pat. No. 6,639,055, US 2000/0705686, U.S. Pat. Nos. 6,500,931, 5,530,101, 5,585,089, 5,693,761, 5,693,762, 6,180,370, US 2003/0229208, US 2003/0389155, U.S. Pat. Nos. 5,714,350, 6,350,861, WO 2010/065921, U.S. Pat. Nos. 5,777,085, 5,834,597, 5,882,644, 5,932,448, 6,013,256, 6,129,914, 6,210,671, 6,329,511, US 2003/0166871, US 2002/0078757, U.S. Pat. Nos. 5,225,539, 6,548,640, 5,624,821, Jones et al., Nature 321 (1986) 522, Verhoeyen et al., Science 239 (1988) 1534, Sims et al., J. Immunol. 151 (1993) 2296, Chothia and Lesk, J. Mol. Biol. 196(1987) 901, Carter et al., Proc. Natl. Acad. Sci. USA 89 (1992) 4285, Presta et al., J. Immunol. 151 (1993) 2623, Padlan, Mol. Immunol. 28 (1991) 489-498, Studnicka et al, Prot. Eng. 7 (1994) 805-814, Roguska, et al., Proc. Natl. Acad. Sci. USA 91 (1994) 969-973 (1994), WO 90/14424, WO 90/14430, WO 90/14443, WO 91/09967, WO 92/001047, WO 92/011272, WO 93/006213, WO 94/018219, WO 99/06834, EP 0 229 246, EP 0 239 400, EP 0 519 596, EP 0 544 809, EP 0 578 515, EP 0 592 106, EP 0 519 596, EP 0 868 504, U.S. Pat. Nos. 4,816,567, 5,225,539, 5,565,332, 5,714,352, 5,723,323, 5,763,192, 5,766,886, 5,814,476, 5,817,483, 5,824,514, 5,976,862, and 6,204,023.

Some humanization approaches used in the art before the current invention are outlined in the following in more detail.

A first approach in the art to reduce immunogenicity of non-human antibodies intended for a therapeutic use in humans was the generation of "chimeric antibodies". Chimeric antibodies are obtained by grafting the complete variable domains of the light and heavy chains of a non-human antibody onto a human constant region (CH1-hinge-CH2-CH3 for the heavy chain variable domain and CL for the light chain variable domain). These chimeric antibodies have a reduced immunogenicity but nevertheless induce an immune response of the recipient (see, e.g., WO 86/01533; U.S. Pat. No. 4,816,567; Morrison, S. L., et al. Proc. Natl. Acad. Sci. USA, 81 (1984) 6851-6855; Morrison, S. L. and Schlom, J., Important Adv. Oncol. (1990) 3-18; Morrison, L., Science 229 (1985) 1202-1207; Oi, V. T. and Morrison, S. L., BioTechniques 4 (1986) 214-221; Gillies, S. D., et al., J. Immunol. Methods 125 (1989) 191-202; U.S. Pat. Nos. 5,807,715; 4,816,397).

US 2003/0054407 disclosed that although a protein may have astronomical number of possible conformations (about $10^{16}$ for a small protein of 100 residues) all antibodies adopt a characteristic "immunoglobulin fold" globally. It was further disclosed that thermodynamic computational analysis can be used for evaluating structural compatibility of a tester sequence with a target structural template. The structural evaluation was based on an empirical and parameterized function and was intended to reduce the number of subsequent in vitro screenings necessary. The function consists of three energy terms: nonpolar salvation, side-chain entropy, and electrostatic energy.

A different approach in the art to reduce immunogenicity was "reshaping". In this approach at first only the HVRs of the non-human antibody (donor antibody; determined according to Kabat) and thereby the "antigen binding properties" of the non-human antibody were transferred onto human variable domains (acceptor antibody). Thereby the corresponding human regions were replaced with the non-human regions. The term "corresponding" denotes a single amino acid residue or a stretch of amino acid residues that is/are positioned across when the respective sequences are aligned. In combination with human constant regions a "humanized antibody" was obtained (see, e.g., EP 0 239

400; U.S. Pat. Nos. 5,225,539; 5,530,101; 5,585,089; WO 91/09967; Jones, P. T., et al., Nature 321 (1986) 522-525; Verhoeyen, M., et al., Science 239 (1988) 1534-1536; Riechmann, L., et al., Nature 332 (1988) 323-327). The success of the grafting depends on the similarity of the three-dimensional structure of the non-human donor antibody and the human acceptor antibody. It was assumed that by having similar three-dimensional structures also the contacts between the HVRs and specific framework residues could be preserved. EP 0 578 515 disclosed a method for producing a humanized monoclonal antibody by utilizing a process of comparative model building. EP 0 592 106 disclosed a method of producing an antibody or fragment thereof which comprises humanized heavy and light chains of a rodent antibody variable region comprising generating sequence alignments, in framework positions only, from relative accessibility distributions from x-ray crystallographic structures of a pool of antibody variable region heavy and light chains to give a set of heavy and light chain surface exposed framework positions.

For grafting human germline, mature or consensus antibody variable regions that have the greatest "homology" are chosen in the art as acceptors. The term "homology", "homolog" or "homologous" denotes a sequence or structural or functional identity (equivalence). Homology can be determined using methods known to a person skilled in the art, such as e.g. FASTA, BLAST (Mount, D. M., (2004) in Bioinformatics: Sequence and Genome Analysis 2nd ed. Cold Spring Harbor Laboratory Press: Cold Spring Harbor, N.Y. ISBN 0-87969-608-7), EMBOSS, MPsrch or Scanps.

A "sequence alignment" can be performed with any method or computer program known to a person skilled in the art. The alignment can be based on sequence and/or structural homology (see, e.g., WO 2012/006490).

Pair-wise alignment methods can be employed in order to identify the best-matching local (fragment sequence) or global (total sequence) alignment of two sequences. The pair-wise alignment can be performed once or multiple times. Pair-wise alignments can be made using different methods known to a person skilled in the art, such as dot-matrix methods, dynamic programming, BLAST2SEQ and word methods.

A multiple sequence alignment is an extension of a pair-wise alignment performed on more than two sequences simultaneously. In a multiple alignment all query sequences are aligned to each other and conserved sequence residues and/or regions are identified.

Local alignments can be made using e.g. the Smith-Waterman algorithm (Smith, T. F. and Waterman, M. S., J. Mol. Biol. 147 (1981) 195-197). Global alignments can be made using e.g. the Needleman-Wunsch algorithm (Needleman, S. B. and Wunsch, C. D., J. Mol. Biol. 48 (1970) 443-453).

The calculation of "homology" or "sequence identity" of two sequences in question can be done as follows: The sequences in question are arranged to result in the best alignment i.e. with the fewest number of mismatches and gaps (gaps can be introduced in one or both sequences). Generally, the part of a reference sequence aligned for comparison purposes is at least 30%, at least 40%, at least 50%, least 60%, at least 70%, at least 80%, at least 90%, or 100% of the total length of the reference sequence. Thereafter the amino acid residues at corresponding positions are compared. If the same amino acid residue is present at a corresponding position in the first sequence and in the second sequence, then the sequences are identical at that position (as used herein amino acid or nucleic acid "iden-tity" is equivalent to amino acid or nucleic acid "homology"). The sequence identity (normally given as percentage value) between two sequences depends on the number of identical positions shared by the two sequences, whereby the number of gaps, and the length of each gap, which had been added to the sequence in order to obtain the best alignment of the two sequences, are taken into account.

Despite sequence alignments also structural alignments can be made e.g. using the DALI method (Holm, L. and Sander, C., Science 273 (1996) 595-603), the SSAP method (sequential structure alignment program; Taylor, W. R., et al., Prot. Sci. 3 (1994) 1858-1870), or the combinatorial extension method.

It has to be pointed out that gaps can be inserted in one, multiple or all aligned sequences at the same or different positions in order to obtain an alignment with increased stretches of sequence identity.

In the "best-fit" method the non-human variable domain in question is aligned with human variable domains. The human sequence that resembles the non-human sequences best is chosen as acceptor (Sims, M J., et al., J. Immunol. 151 (1993) 2296-2308; Chothia et al., J. Mol. Biol. 196 (1987) 901-917).

In the "consensus" method a particular framework sequence is derived from the consensus sequence of all human antibodies of a particular subgroup of light or heavy chains. For example, the consensus sequence can be derived from the most abundant human subclasses, VL6 subgroup I (VL6I) and VH subgroup III (VHIII) (Carter, P., et al., Proc. Natl. Acad. Sci. USA 89 (1992) 4285-4289; Presta, L., et al., J. Immunol. 151 (1993) 2623-2632).

In another approach in the art human framework sequences are chosen from the set of human germline genes based on the structural similarity of the human CDRs to those of the mouse antibody to be humanized. The structural similarity is evaluated by scoring residue-to-residue homology of the mouse CDRs to human candidates with the same Chothia canonical structures. No mutations of the human framework are introduced whatsoever (see e.g. Hwang, W. Y. K., et al. Methods 36 (2005) 35-42).

It was assumed in the art that the more homologous the humanized antibody is compared to the non-human antibody the smaller the risk would be that the introduction of the non-human CDRs into the selected human framework also introduces distortions of either the CDRs or the frameworks resulting in a reduction or even complete loss of the antigen binding properties of the humanized antibody.

Thus, in the art at first variable domains were selected as acceptor sequences that had a sequence identity (excluding the CDRs) above a threshold value. This threshold could be as low as 65% but also up to 80% or more. But it turned out that it was in most cases not possible to transfer the binding characteristics of the non-human antibody to the humanized antibody by simple grafting of the CDRs. Frequently back-mutations of additional residues in the CDRs or the framework of the non-human antibody were necessary to restore the binding characteristics at least in part. The additional residues were required to preserve the CDR three-dimensional conformation. As the additionally transferred residues are mutations within the chosen acceptor antibody they are termed "back mutations" (see e.g. Kabat, E. A. and Wu, T. T., J. Immunol. 147 (1991) 1709-1719; Queen, C., et al., Proc. Natl. Acad. Sci. USA 86 (1989) 10029-10033; Co, M. S. and Queen, C., Nature 351 (1991) 501-502; Tempest, P. R., et al., Biotech. 9 (1991) 266-271; WO 92/04381).

The term "backmutation" or "back to [non-human species] mutation" denotes an amino acid residue that is reverted back from the human residue to the non-human species residue in order to improve the properties of the humanized antibody. This could also be a somatically mutated amino acid, which is replaced with the corresponding germline residue. To identify candidate residues for backmutation the amino acid sequence of a primary humanized antibody is aligned with the respective germline sequence, e.g. obtained from the VBASE database (VBASE is a comprehensive directory of all human germline variable region). Each amino acid residue identified as a candidate residue for backmutation has to be examined for a direct or indirect involvement in antigen binding. Amino acid residues identified (e.g. after mutation) to be able to modify a characteristic of the humanized antibody should be reverted back to the non-human residue.

Nevertheless, the binding affinity of the antibody humanized by the art methods using grafting is normally significantly reduced compared to the non-human antibody. However, the determination of which non-human residues should be introduced to obtain humanized antibodies with binding efficiencies similar to the non-human antibody are difficult to predict, being largely empirical and cannot be taught.

It has been outlined in the art that framework residues, which are unusual in the non-human antibody and close to the antigen binding residues, or which are packing residues, or residues in the so called Vernier-Zone, as well as those close to the antigen are important residues (see e.g. Martin and Thornton, J. Mol. Biol. 263 (1996) 800-815; Foote et al., J. Mol. Biol. 224 (1992) 487-499).

WO 90/07861 disclosed four rules for designing humanized antibodies: 1) homology between human acceptor and non-human donor sequences; 2) use donor rather than acceptor amino acids where the acceptor amino acid is unusual at that position; 3) use donor framework amino acids at positions adjacent to the CDR; 4) use donor amino acids at framework positions where the side chain atom is within 3 Angstroms of the CDR in a 3-D model.

Another humanization approach in the art is "SDR grafting". This approach is based on the finding that a lower number of amino acid residues than those forming the CDRs actually make contact with the antigen and, thus, determine the binding specificity of an antibody. These residues were termed "specificity determining residues (SDRs)". They account for about one third of the total CDR residues. Only those residues are transferred in the grafting process (see e.g. Padlan et al., FASEB J. 9 (1995) 133-139; Kashmiri et al., Methods 36 (2005) 25-34).

A further approach in the art for humanizing of non-human antibodies is "veneering" (also denoted as "resurfacing") (see e.g. EP 0 592 106; EP 0 519 596; Studnicka, et al., Prot. Eng. 7 (1994) 805-814; Roguska, et al., Proc. Natl. Acad. Sci. USA 91 (1994) 969-973; WO 2004/016740). By analyzing human and murine antibodies specific surface/solvent exposed amino acid residues could be determined. A surface residue has generally a relative solvent accessibility that is 30% or more (see e.g. Pedersen, J., et al., Mol. Biol. 235 (1994) 959-973). It was disclosed that specific surface positions have a preference for a specific limited number of residues (see e.g. Padlan, et al., Mol. Immunol. 28 (1991) 489-498; Pedersen, et al., J. Mol. Biol. 235 (1994) 959-973; Roguska et al., Prot. Eng. 9 (1996) 895-904). By replacing exposed residues in non-human antibodies that differ from the human residues immunogenicity might be reduced as immunogenicity seems to be correlated with surface characteristics. With this approach it is intended to mask the murine antibody by providing it with a humanized surface (see e.g. Mark, et al., Handbook of Experimental Pharmacology Vol. 113, Springer, 105-134 (1994)).

A further approach in the art is denoted as "superhumanization". This approach includes the acts of obtaining a peptide sequence for a subject variable region encoded by a non-human mature antibody gene and identifying a first set of canonical CDR structure types for at least two CDRs within the non-human antibody variable region. Then a library of peptide sequences for human antibody variable regions for human antibodies is obtained. In the next step canonical CDR structure types (i.e., a second set of canonical CDR structure types) for at least two CDRs for each sequence within the library of human variable region sequences are identified. From this library there is selected a subset of candidate sequences by comparing the first set of canonical CDR structure types to the second set of canonical CDR structure types (i.e., comparing the mouse canonical CDR structure types to the human canonical CDR structure types at corresponding locations within the variable region) and selecting those human sequences where the second set of canonical CDR structure is the same as the first set of canonical CDR structure types for the CDR sequences at corresponding locations within the non-human and human variable regions, respectively. The method uses these candidate human variable region sequences as a basis for constructing a chimeric molecule that includes at least two of the CDR sequences from the non-human variable region (e.g., of the mouse CDRs) combined with the framework regions from candidate human variable region sequences. The result of this is that the chimeric antibody contains each of the non-human CDR sequences substituted for each of the human CDR sequences at corresponding locations in the variable regions so that the framework sequences in the chimeric antibody differs from the candidate human framework sequences by no more than 10 amino acid residues (see WO 2004/006955; Tan, P., et al., J. Immunol. 169 (2002) 1119-1125).

Another method from the art for antibody humanization is based on a metric of antibody humanness termed Human String Content (HSC). This method compares the mouse sequence with the repertoire of human germline genes and the differences are scored as HSC. The target sequence is then humanized by maximizing its HSC rather than using a global identity measure to generate multiple diverse humanized variants (Lazar et al, Mol. Immunol. 44 (2007) 1986-1998).

Another approach in the art is "framework shuffling". In this approach individual frameworks from all known frameworks are combined with the respective non-human CDRs and any combination of four frameworks with the three CDRs are expressed and screened (Dall'Acqua, W. F., et al., Methods 36 (2005) 43-60; Damschroder, M. M., et al., Mol. Immunol. 44 (2007) 3049-3060).

Another approach in the art is "humaneering". Herein the minimum specificity determinants (MSDs) are experimentally determined using sequential exchange of individual non-human regions of the variable domains with human counterparts and screening of the binding of the members of the respective partially humanized antibody library. This can be accomplished by transferring the minimal essential binding specificity in the context of transferring a D segment, or a CDR3, or a CDR3-FR4, or any other CDR3-FR4 fragment that comprises the minimal essential binding specificity determinant. It was assumed that with this method the binding epitope is retained and antibodies that are 91-96% homologous to human germline gene antibodies can be isolated (see e.g. WO 2005/069970).

Thus, from the above it can be seen that the term "humanized antibody" as used in the art denotes an antibody comprising the minimal number of amino acid residues from a non-human antibody, but having a comparable antigen specificity and affinity as the non-human antibody and at the same time the humanized antibody has no or only a very low immunogenicity when applied to a human being.

Another approach in the art is based on the analysis and comparison of three-dimensional models of the non-human antibody and different humanized antibody variants, to identify the likely role of residues with respect to antigen binding. Thereby donor residues might be identified relating to the binding characteristics of the non-human antibody.

Around 1990 the first modeling approaches were employed in the art to address the problem of reduced affinity of the humanized antibody. This was a two-step approach for selecting the human framework regions based on amino acid sequence homology and alignment of putative CDR contact residues from the non-human antibody by tertiary structure modeling (see e.g. Queen, C., et al., Proc. Natl. Acad. Sci. USA 86 (1989) 10029-10033; Co, M. S., et al., Proc. Natl. Acad. Sci. USA 88 (1991) 2869-2873; WO 90/07861; U.S. Pat. Nos. 5,693,762; 5,693,761; 5,585,089; 5,530,101).

The three-dimensional structure of the variable domains and thereby the three dimensional conformation of the CDRs is made up of amino acid-amino acid interactions, such as ionic interactions, hydrogen bonds or hydrophobic interactions.

The different amino acid residues have due to their structure different properties and, thus, changes from one amino acid residue to a different amino acid reside can affect the three dimensional structure/stability of the variable domain and thereby the characteristics of the humanized antibody.

For example, the replacement of the amino acid residue glycine with the amino acid residue alanine introduces a new CH3 group and thereby reduces the possible orientations of this amino acid residue due to the increased spatial demand, thereby reduces the conformational flexibility and increases the entropy of unfolding resulting in an improved conformational stability of the variable domain (Manning, M. C., et al., Pharm. Res. 6 (1989) 903-917).

Protein folding is initiated by the formation of hydrophobic interactions.

Individual amino acid residues, amino acid sequence stretches or polypeptide regions can be characterized as being hydrophilic or hydrophobic. Black and Mould (Anal. Biochem. 193 (1991) 72-82) defined the following hydrophobicity sequence for the individual amino acid residues (most hydrophobic to most hydrophilic):

Phe>Leu=Ile>Tyr=Trp=Val>Met>Pro>Cys>Ala>
Gly>Thr>Ser>Lys>Gln>Asn>His>Glu>Asp>Arg.

The scaled values for hydrophobicity as reported by Black and Mould are recited in the following Table.

| amino acid | hydrophobicity value |
|---|---|
| A, Ala | 0.616 |
| C, Cys | 0.68 |
| D, asp | 0.028 |
| E, Glu | 0.043 |
| F, Phe | 1 |
| G, Gly | 0.501 |
| H, his | 0.165 |
| I, Ile | 0.943 |
| K, Lys | 0.283 |
| M, met | 0.738 |

-continued

| amino acid | hydrophobicity value |
|---|---|
| N, Asn | 0.236 |
| P, pro | 0.711 |
| Q, Gln | 0.251 |
| R, Arg | 0 |
| S, Ser | 0.359 |
| T, Thr | 0.45 |
| V, Val | 0.825 |
| W, Trp | 0.878 |
| Y, Tyr | 0.88 |
| Asx | 0.132 |
| Glx | 0.147 |

The three dimensional orientation of amino acid residues can be assumed to be a "standard geometry" based on bond lengths and angles from small molecule structures (see e.g. Weiner, S. J., et. al., J. Amer. Chem. Soc., 106 (1984) 765-784).

In the "homology modeling" approach a computational three-dimensional approximation or model of an antibody is generated based on the known three-dimensional structure of a reference antibody. As the reference antibody and the antibody in question have a related three-dimensional structure an alignment between the reference antibody and the antibody in question can be generated. The amino acid sequences of these two antibodies are aligned and the three-dimensional coordinates of identical sequence stretches are directly transferred from the reference antibody to the antibody in question. In case of non-identical portions of the two antibodies (i.e. stemming from different amino acid residues, insertions or deletions) the three-dimensional coordinates are determined based on generic structural templates with energy refinement. Homology modeling can be used to identify residues of the non-human antibody that potentially are involved in supporting the structure of the binding site formed by the CDRs (see, e.g., Kolinski et al., Proteins. 37 (1999) 592-610; Rost et al., Protein Sci. 5 (1996) 1704-1718; U.S. Pat. Nos. 7,212,924; 6,256,647; 6,125,331; Xiang, et al., Curr. Prot. Pept. Sci. 7 (2006) 217-227).

The alignment of different three-dimensional structures can be made by superimposing one on the other. Therefore, for example, one is three dimensionally fixed and the other is rotated and translated in space, in order to orientate the secondary structural elements of alpha-helices and beta-sheets to have them as congruent (similar/close in spatial position and orientation) to one another as possible.

After the alignment, the distance between the alike primary carbon atoms (Cα's) is calculated for each amino acid residue. Based on these distances it can be evaluated which of the amino acid residues have the same position and which have different positions. Generally, if the Cα-Cα distance for an amino acid residue is 1.0 Å or below, that position can be deemed three dimensional similar or even identical, and if the Cα-Cα distance for an amino acid residue is more than 1.0 Å that position can be deemed three dimensional different.

In order to further improve the alignment, it is possible to subject the model to energy minimization wherein the Cα coordinates are fixed (otherwise, the alignment would be worsening again). Thereby "unusual" bond lengths and angles that have been introduced during the formation of the alignment can return to a standard (chemically acceptable) geometry.

The likelihood that an identified framework amino acid residue influences the binding characteristics of the humanized antibody is dependent on the spatial distance. Based on the structural model the residues identified to potentially interfere with antigen binding are ranked based on the spatial distance from residues in the CDRs. Generally, residues that are within 4.5 Å of any CDR atom are considered potentially interacting residues.

Nowadays three-dimensional immunoglobulin models are commonly available and are familiar to persons skilled in the art. The three-dimensional configurations of the different classes of immunoglobulins are known (see, e.g., Abbas et al. Cellular and Mol. Immunology, 4th ed., W.B. Saunders, Co., (2000)). With the aid of specified computer programs, it is possible to display calculated three-dimensional conformational structures of antibody variable domains (see e.g. U.S. Pat. No. 5,821,337). Crystal structure databanks (e.g. Protein Data Bank, pdb) can be used as source of the structures (see e.g. Bernstein, F. C., et al., J. Mol. Biol., 112 (1977) 535-542).

WO 2006/096653 disclosed a method of humanizing an immunoglobulin (Ig) variable region which comprises a) variable region framework (FR) amino acid residues from an acceptor immunoglobulin variable region and b) complementarity determining regions (CDRs) from a non-human donor immunoglobulin variable region, the method comprising, i) providing data which allows prediction of a 3-D conformation of at least one CDR; ii) identifying which FR amino acid residues are predicted to affect the 3-D conformation of the at least one CDR; iii) identifying at least one candidate donor CDR amino acid residue for substitution with an elected amino acid residue, wherein the elected amino acid residue conformationally accommodates a FR amino acid residue difference between the donor immunoglobulin variable region and the acceptor immunoglobulin variable region without affecting the CDR conformation: and iv) substituting the at least one candidate donor CDR amino acid residue with the elected amino acid residue to form a humanized immunoglobulin variable region. Also disclosed therein is a method of designing a humanized immunoglobulin variable region which comprises a) variable framework regions (FRs) from an acceptor immunoglobulin variable region and b) complementarity determining regions (CDRs) from a non-human donor immunoglobulin variable region, the method comprising, (a) identifying framework region (FR) amino acids which differ between the acceptor immunoglobulin variable region and the donor immunoglobulin variable region; (b) identifying amino acids adjacent to the FR amino acid(s) identified in step (a); (c) identifying at least one candidate amino acid from the amino acids identified in step (b) for substitution with an elected amino acid residue which conformationally accommodates the FR amino acid(s) identified in step (a).

US 2006/0258852 disclosed an exemplary approach to redesigning the variable region sequences (e.g. CDR sequences, and optionally FR sequences) by using structure-based computational design methods. The identity of the residues in the flexible zone is fixed to acceptor residues, but their 3-dimensional positions are allowed to change during the calculation. The residues in the mutation zone are allowed to change both their amino acid identity and conformation. All residues in the CDRs outside of the mutation zone are donor, and all residues in the FR outside of the mutation zone are acceptor. In this method, the candidate residues (e.g. CDR residues, and optionally FR residues) that have side chains that are geometrically close (e.g. within about 4-25 Å of such regions, in particular <5 Å distance) to one or more of the important residue differences in the framework (as identified in step 2), are simultaneously mutated computationally to all possible 3-dimensional conformations (rotamers) of any of the 20 naturally occurring amino acids and the resulting mutants are evaluated computationally. One such method is known as side chain repacking method. In a side chain repacking calculation, the candidate amino acid residues can be modified computationally, and the stability of the resulting polypeptide mutants evaluated computationally. The side chain repacking calculation generates a ranked list of the variants that have altered stability (i.e., altered intramolecular energy). Mutants which result in low free energy, and which are confirmed as conformationally accommodating by visual inspection of a 3-dimensional model, can then be selected for experimental expression. The list of computationally generated mutants can be sorted by calculated stability of the mutant in order to generate a list of variants that will be expressed experimentally. In the calculations the protein backbone is allowed very little or no flexibility, which ensures that the designed mutants are predicted to be stable with the given CDR conformations. Thus, the computational analysis allows one to predict structurally compatible sequences, in particular CDR sequences, with given FR domains within a variable region.

WO 2007/109742 disclosed a method of designing a humanized immunoglobulin comprising the steps of a) determining the three dimensional structure of a parent antibody variable domain or a parent antibody variable domain bound to hapten; b) identifying the specificity determining residues (SDR) of said parent structure; c) dividing said structure into sections comprising the six complementarity determining region (CDR) loops and the framework region (FR) comprising both heavy and light chains; d) superimposing the three dimensional structures of said sections onto a defined database of corresponding three dimensional CDR loop and framework structures of human acceptor antibodies; e) grafting parental SDR into a selected acceptor structure to determine a model of the amino acid sequence of said humanized immunoglobulins; f) calculating the energy value for amino acid residue substitutions; g) optimizing the amino acid sequence of said humanized immunoglobulins by choosing residues with negative energy values; and h) designating the amino acid sequences of humanized immunoglobulin variable region segments.

Generally, in the art variable domains of a specific similarity (e.g. >70% sequence homology) are selected from the database and used for the generation of a homology model.

Worn, A. and Plueckthun, A. (J. Mol. Biol. 305 (2001) 989-1010) reported that the stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (see, e.g., US 2012/0064095).

It is the aim of the humanizing scientist to provide humanized antibodies with, e.g., reduced immunogenicity, optimized antigen binding, affinity, avidity and/or half-life.

Different humanization variants are produced and evaluated by suitable screening methods. There are different known methods for antibody screening, such as e.g. in vitro assays, in vivo and cell-based assays, and selection methods. Generally, such an assay is a binding assay in which the antibody binds to its target and either the binding is determined or an effect initiated by the binding is determined.

The determination of the binding in a binding assay can be performed using different methods, such as e.g. FRET (Fluorescence Resonance Energy Transfer), BRET (Bioluminescence Resonance Energy Transfer)-based assays, Alpha Screen® (Amplified Luminescent Proximity Homogeneous Assay), Scintillation Proximity Assay, ELISA (Enzyme-Linked Immunosorbent Assay), SPR (Surface Plasmon Resonance), isothermal titration calorimetry, differential scanning calorimetry, gel electrophoresis, and chromatography including gel filtration.

One preferred method for the screening of antibodies based on their binding affinity is surface plasmon resonance (SPR). This method especially allows the determination of the association rate ($k_a$, $k_{on}$) and the disassociation rate ($k_d$, $k_{off}$) of the binding event (see e.g. Jonsson and Malmquist, Advances in Biosensors, 2(1992) 291-336; Wu et al. Proc. Natl. Acad. Sci. USA, 95 (1998) 6037-6042).

Different methods for the screening and selection of antibodies are known, such as e.g. phage display (Phage display of peptides and proteins: a laboratory manual, Kay et al., Academic Press, San Diego, Calif., (1996); Lowman et al., Biochemistry 30 (1991) 10832-10838; Smith, Science 228 (1985) 1315-1317), selective phage infection (Malmborg et al., J. Mol. Biol. 273 (1997) 544-551), selectively infective phage (Krebber et al., J. Mol. Biol. 268 (1997) 619-630), delayed infectivity panning (Benhar et al., J. Mol. Biol. 301 (2000) 893-904), cell surface display (Wittrup, Curr. Opin. Biotechnol., 12 (2001) 395-399), bacterial display (Georgiou et al., Nat. Biotechnol. 15 (1997) 29-34; Georgiou et al., Trends Biotechnol. 11 (1993) 6-10; Lee et al., Nat. Biotechnol. 18 (2000) 645-648; June et al., Nat. Biotechnol. 16 (1998) 576-580), yeast display (Bader & Wittrup, Methods Enzymol. 328(2000) 430-444; Boder & Wittrup, Nat. Biotechnol. 15 (1997) 553-557), and mammalian cells (Whitehorn et al., Biotechnol. 13 (1995) 1215-1219), in vitro display (Amstutz et al., Curr. Opin. Biotechnol. 12 (2001) 400-405), polysomic display (Mattheakis et al., Proc. Natl. Acad. Sci. USA 91 (1994) 9022-9026), ribosome display (Hanes et al., Proc. Natl. Acad. Sci. USA 94 (1997) 4937-4942), mRNA display (Roberts & Szostak, Proc. Natl. Acad. Sci. USA 94 (1997) 12297-12302; Nemoto et al., FEBS Lett. 414 (1997) 405-408), and ribosome-inactivation display system (Zhou et al., J. Am. Chem. Soc. 124 (2002) 538-543), periplasmic expression and cytometric screening (Chen et al., Nat. Biotechnol. 19 (2001) 537-542), the protein fragment complementation assay (Johnsson & Varshavsky, Proc. Natl. Acad. Sci. USA 91 (1994) 10340-10344; Pelletier et al., Proc. Natl. Acad. Sci. USA 95 (1998) 12141-12146), the yeast two hybrid screen (Fields & Song, Nature 340 (1989) 245-246; Visintin et al, Proc. Natl. Acad. Sci. USA, 96 (1999) 11723-11728).

Solubility and overall structural integrity of an antibody for example can be quantitatively or qualitatively determined by methods such as, e.g., gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay, X-ray crystallography, and NMR spectroscopy.

A humanization is carried out in general as follows:
1. Selection of human or humanized or consensus antibody frameworks
   alignment of the non-human variable domain sequence against a library of human/humanized/consensus variable domain sequences (e.g. obtained from VBASE or NCBI)
   selection of acceptor frameworks based on amino acid sequence homology
2. Refinement
   based on either available crystal structure information or homology modeling identification of critical residues in the non-human antibody, especially in the framework, that support the structure of the binding site, VH-VL pairing, etc.
   backmutation of the identified critical residues.

Thus, as can be seen from the above it is highly important during the humanization of a non-human antibody to identify residues influencing the antigen binding and how to modify them in order to regain lost properties in the humanized antibody.

Although a lot of different approaches have been developed for the humanization of non-human antibodies, no generally applicable method for designing a humanized antibody has been established yet. Due to that multiple attempts are required to obtain a humanized antibody with the desired properties, such as, e.g., several variant humanized antibodies have to be generated and evaluated to identify the best humanized variant.

Embodiments of the Invention

Herein is reported a method for humanizing non-human antibodies using a structure-based approach. With the method reported herein it is possible to determine (the requirement for and) the suitability of specific (back- or forward-)mutations of amino acid residues at defined positions of a selected acceptor sequence, such as, e.g., a human germline sequence. The topology, the three-dimensional structure and the interactions of the respective residue as well as the nature of its replacement are considered. Thereby the influence on antigen binding of a specific amino acid residue change is reflected. This reduces or even prevents an interference with antigen binding in the humanized sequence due to a change of a specific amino acid residue. Thereby an improved humanization method is provided.

The method comprises the following central or core steps:
alignment and ranking of the amino acid sequence to be humanized with all potential acceptor sequences; ranking can be done on similarity or at the end on scores/score on acceptor sequences/score on final sequences, i.e. a bunch of humanization (suggestion) candidates can be ranked;
optionally assigning the canonical loop structure to further identify more important structural influencing residues;
optionally search in protein data bank (PDB) to get a starting point for building a model;
build a model; this is required to attribute (final) scores; this includes a search to identify substructures with the same topology that lead to the model with high accuracy; thus, a three-dimensional search is performed to have a three-dimensional environment dependent model built;

check alignment for insertions, for deletions and, if present, for particular segments with lower homology;

if the HVR differs in the built model from the HVR in the found structure a search is done in the structure database for each HVR loop separately or even only for ascending and descending loop parts of each HVR;

VH/VL-orientation adjustment; VH/VL-orientation has been demonstrated as important to arrange the HVR residues with the right distance between HVR-Hs and HVR-Ls; the relative orientation is triggered mainly by residues at the interface between VH and VL; these can be framework residues as well as HVR residues;

energy minimization of the model; recommended to relax the system but not essential assign scores for each change/difference based on the topology sorting of proposed sequences based on individual or overall scores select germline of choice; if similar overall scores, then frequently used germline should be chosen/preferred decide on V and J combination based on the scoring decide on required backmutations to eliminate most or all of 4 or 4 and 3 scores; this can lead to several variants with some 3 scores instead of none or all of them; considering changes for which the score is 1 or 2 and considering forward mutations for which the score is also low.

It has been found that the humanized antibodies obtained with the method as reported herein have more humaneness (human character) compared to humanized antibodies obtained with conventional methods, which are not using the topological effect considerations according to the method of the current invention. Without being bound by this theory it is assumed that this is due to the fact that in the art longer, non-interrupted stretches are taken from the human germline sequence. By using smaller sub-structures as in the method according to the current invention an improved model can be build and improved humanized antibodies can be obtained.

The inventive method comprises the step of quantifying (by obtaining a score for) each/any amino acid difference between an acceptor sequence (e.g. a human germline sequence), which has been selected for the transfer of the hypervariable regions of the non-human antibody, and the non-human antibody itself, which is based on the three-dimensional structure, the topology and the interactions of the respective residue with its environment.

For quantifying the topological difference and its effect the structural difference between the amino acid residues and the topology of the respective position based on the three-dimensional structure, e.g. determined using a three-dimensional homology model, is taken into account. It has to be pointed out that for certain positions two or more topology identifiers can be assigned. Generally, only the most important is used. The topology identifiers according to the current invention have the following gradation: A first, then L, then S or C (depending on the topological influence; e.g. a contact position C can be more influencing than salt bridge far away from an A residue), then I, then E. The structural difference is reflected in a score. The magnitude of the score is influenced/determined by the impact of the amino acid difference on framework stability or HVR conformation: wherein 0 denotes no influence, 1 denotes slight influence, 2 denotes moderate influence, 3 denotes a potentially affected framework stability and 4 denotes that framework stability or HVR conformation will severely be disturbed/influenced.

The structural difference can be determined for each amino acid of the 20 naturally occurring amino acid residue, to be more precise for the 19 different amino acid residues, if assumed to be present at the respective position. It can also be linked to the (more limited number of different) amino acid residues that are present at said position in the human germline sequence. Thereby a (scoring) matrix reflecting the resulting (overall) structural differences is obtained.

The invention is based at least in part on the finding that based on the identified structural difference a suitable amino acid change can be identified, if required. This difference/change results in a different, preferably lower, structural distortion (e.g. a reduced influence on/deformation of the framework/HVR conformation) and thereby an increased binding of the humanized antibody to its target. Thereby a humanized antibody with improved properties can be provided when a method according to the current invention is used. For example, the reduction of the binding affinity of the humanized antibody can be minimized.

One aspect as reported herein is a method for producing an antibody comprising the following steps:

a) sequencing (the amino acid sequence of or the nucleic acid sequence encoding) the variable domains of a non-human antibody and thereby obtaining the amino acid sequence of the variable domains of the non-human antibody, b) optionally generating a three-dimensional homology model of said non-human antibody, c) identifying and selecting as variable domain acceptor sequence for each variable domain (independently of each other for i) and ii) and depending on each other for iii) and iv))
  i) a human germline sequence with the highest sequence homology to the respective non-human antibody variable domain, or
  ii) two or more human germline sequence fragments forming together a complete variable domain that, when aligned, have a sequence homology higher than a single human germline sequence to the respective non-human antibody variable domain, or
  iii) human germline amino acid sequences that allow maintaining heavy chain variable domain to light chain variable domain angle (VH/VL angle) of the non-human antibody,
  iv) a VH/VL pair of a human or humanized antibody, d) grafting the HVR/CDR residues of the non-human antibody on the acceptor sequences selected in step c), e) quantifying the structural difference (by scoring the amino acid residue differences) between the non-human antibody and the sequences selected in step c) or the sequences obtained in step d), f) introducing based on the quantifying of the previous step amino acid (backward- and forward-)mutations in the selected sequences or the grafted sequences, (mutating based on the quantifying/scoring of the previous step the amino acid sequences of step c) or step d)), g) synthesizing or generating nucleic acid sequences encoding the amino acid sequences obtained in f), h) cultivating a cell comprising the nucleic acids of g) and thereby producing the antibody.

In one embodiment this method is further performed only for a non-human antibody light chain variable domain or a non-human antibody heavy chain variable domain.

One aspect as reported herein is a method for synthesizing or producing or providing a nucleic acid sequence encoding an immunoglobulin variable domain comprising the following steps a) aligning the amino acid sequence of a non-human antibody heavy chain or light chain variable domain
with
a first humanized variant of said non-human antibody heavy chain or light chain variable domain obtained by grafting the CDRs or hypervariable regions (HVRs) or specificity determining residues (SDRs) of a non-human antibody heavy chain or light chain variable domain on
i) a human germline amino acid sequence with the highest sequence homology to the respective non-human antibody heavy chain or light chain variable domain,
or
ii) two or more human germline amino acid sequence fragments forming a complete variable domain that, when aligned, have a homology higher than a single human germline amino acid sequence to the respective non-human antibody variable domain,
or
iii) a human germline amino acid sequence that allows maintaining VH/VL angle of the non-human antibody variable domain,
or
iv) a heavy chain or light chain of a human or humanized antibody,
(to achieve maximal level of amino acid sequence identity),
b) quantifying the three-dimensional difference of (or in) aligned framework positions in which the non-human heavy chain or light chain variable domain and the first humanized variant of said non-human heavy chain or light chain variable domain have different amino acid residues, (which, due to the difference, influence antigen binding and/or three dimensional structure,)
c) modifying (i.e. mutating) the first humanized variant of said non-human heavy chain or light chain variable domain amino acid sequence by replacing one or more amino acid residue determined in step b) with amino acid residue(s) that influences antigen binding and/or three dimensional structure to a lesser extent than the replaced amino acid residue(s) (, i.e. have a lower score), to obtain a new humanized variant of said non-human heavy chain or light chain variable domain with reduced three-dimensional difference,
d) optionally repeating steps b) and c) with the new humanized variant obtained in step c) as first humanized variant until the three-dimensional difference is no longer changing/can no longer be reduced/is less than 10% as determined by RMSD analysis,
e) synthesizing or producing or providing a nucleic acid sequence encoding the modified variable domain obtained in step c) or d).

One aspect as reported herein is a method for producing an immunoglobulin comprising the following steps
a) individually for the heavy chain variable domain and light chain variable domain
aligning the amino acid sequence of a non-human heavy chain or light chain variable domain
with
a first humanized variant of said non-human heavy chain or light chain variable domain obtained by grafting the CDRs or hypervariable regions or specificity determining residues of a non-human antibody heavy chain or light chain variable domain on
i) a human germline amino acid sequence with the highest sequence homology to the non-human variable domain,
or
ii) two or more human germline amino acid sequence fragments that when aligned have a homology higher than a single human germline amino acid sequence,
or
iii) a human germline amino acid sequence that allows maintaining VH/VL angle,
or
iv) a human or humanized antibody heavy chain or light chain variable domain,
(to achieve maximal level of amino acid sequence identity),
quantifying the three-dimensional difference of/in aligned framework positions in which the non-human heavy chain or light chain variable domain and the first humanized variant of said non-human heavy chain or light chain variable domain have different amino acid residues, (which due to the difference influence antigen binding and/or three dimensional structure,)
modifying/mutating the first humanized variant of said non-human heavy chain or light chain variable domain amino acid sequence by replacing one or more amino acid residue determined in the previous step (with an amino acid residue that influences antigen binding and/or three dimensional structure less than the replaced amino acid residue, (i.e. have a lower score,)) to generate a modified variable domain with reduced three-dimensional difference,
optionally repeating the two previous steps with the modified variable domain as first humanized variant until the three-dimensional difference is no longer changing/can no longer be reduced/is less than 10% as determined by RMSD analysis,
synthesizing/producing/providing a nucleic acid sequence encoding the modified variable domain obtained in the previous step.
b) cultivating a mammalian cell comprising the nucleic acid encoding an immunoglobulin heavy chain comprising the nucleic acid encoding the modified heavy chain variable domain of step a) and the nucleic acid encoding an immunoglobulin light chain comprising the modified light chain variable domain of step a) for the expression of the immunoglobulin,
c) recovering the immunoglobulin from the mammalian cell or the cultivation medium and thereby producing an immunoglobulin.

The influence of an amino acid difference between a non-human antibody and its humanized variant on antigen binding and/or three-dimensional structure can be quantified with the scoring approach as reported herein.

For the quantification of the three-dimensional difference, i.e. for the scoring, all amino acid residues are characterized based on their position in the three-dimensional structure, e.g. obtained from a homology model.

First, the amino acid residues are classified as follows based on their topology:
I: internal side chain,
E: external side chain,
C: contact H-L chains,
A: antigen contact,
L: linker to antigen,
S: participating in a salt bridge,
N: no particular interaction.

It has to be pointed out that for certain residues more than one topology identifier as shown above can be assigned. Generally, the more important is chosen. The topology identifiers according to the current invention have the following gradation: A first, then L, then S or C (depending on the topological influence; e.g. a contact position C can be more influencing than salt bridge far away from an A residue), then I, then E.

Thus, in one embodiment of any method according to the current invention the quantifying the effect of the different amino acid residue in aligned framework positions is done by using the three-dimensional structure of the VH and/or VL. In one embodiment the three-dimensional structure is obtained by X-ray crystallography or by homology modeling. In one embodiment the generation of a three-dimensional model of the non-human variable domains or the non-human antibody is by homology modeling. In one embodiment the homology modelling is done using a model generated based on substructures of the entire sequence. In one embodiment the substructure comprises at most complete regions of the variable domain. In one embodiment the substructure comprises at most 20 amino acid residues. In one embodiment the substructure comprises at most 15 amino acid residues. In one embodiment the substructure comprises at most 10 amino acid residues. In one embodiment the substructure comprises 10 or less amino acid residues. In one embodiment any method according to the invention further comprises prior to the quantifying the step of assigning to the respective positions one of the topology classifiers I (internal side chain), E (external side chain), C (contact heavy-light chains), A (antigen contact), L (linker to antigen), S (participating in a salt bridge), or N (none of the other=no particular interaction). The homology model used in the method as reported herein is built in one embodiment for each framework region, HVR and conjunction of framework and HVR separately.

From the art different topology classifiers are known, such as e.g. the group comprising Strall (structure all) positions (=all residues within 5 Angstrom from either VH-VL interface or close to CDR residues), Buried (=solvent exposure below 20% in model vs in GXG)) and Strltd (=particular residues making hydrophobic, electrostatic, or ionic, interactions with CDR or at the interface). These topology classifiers are defining only CDR residues and additionally particular residues at the interface or in contact with CDR residues.

In contrast thereto the classification reported herein does automatically influence the resulting score. This provides additional information, e.g. when the score is high there is shown the need to introduce a backmutation to secure antibody integrity. The topology identifiers according to the current invention have the following gradation: A first, then L, then S or C (depending on the topological influence; e.g. a contact position C can be more influencing than salt bridge far away from an A residue), then I, then E.

In more detail, if a residue in the HVR is of topology A, then a change is assigned a score of 4, i.e. it is highly influencing the structure and therefore it is highly risky to change it;

if a residue of the topology L has also the topology S, then a change is assigned a score of 4 rather than a 3 for some changes because it accumulates topological importance;

if a residue of the topology C (contact between VH and VL) or A (potentially being in contact with the antigen) or L (linker residues between "A" residues and framework residues), a higher score due their potential effect on VH-VL destabilization or on the orientation/conformation of the A residue is assigned to a change; in other words, for the 3 categories A, C, and L, a forward mutation in HVRs gets a high score as well as a back mutation in framework avoids getting a high score;

if a residue of the topology C, has a short side chain not making contact with the neighbored variable domain its replacement by a smaller amino acid will get a score of 1 or 2 compared to other replacements with bigger amino acid side chain which can be scored a 2 or 3 depending on the size of the side chain and of the nature of the contact with the neighbored variable domain;

if a residue of the topology C, has a short side chain not making contact with the neighbored variable domain and the replacement takes place with a side chain that is so huge that the accommodation for such side chain can only be achieved by a change of the VH-VL orientation, this change will be scored 4;

if a residue of the topology C has also the topology S, then a change is assigned a score of 4 rather than a 3 for changes because its accumulate topological importance;

if a residue of topology S has also the topology I, then a change is assigned a score of 4 or 3, respectively for side chain of inverted charge and for neutral smaller side chain that only lack the appropriate charge;

if a residue of topology S has also the topology I and the replacement takes place with a neutral but bigger side chain, then the change is assigned a score of 4 as steric hindrance occurs between the replaced side chain and the charged residue in front of it;

if a residue of topology S has also the topology E, then a change is assigned a score of 3 or 2, respectively for side chain of inverted charge and for any side chain that only lack the appropriate charge.

If there is a difference between the amino acid residue in the framework of the non-human variable domain and the (first) humanized variant of the non-human heavy chain or light chain variable domain the difference can be quantified, i.e. by assigning a score. The replacement by a similar (physically, volumetric) amino acid normally results in a lower score, i.e. is usually tolerated, while completely changing the side chain characteristics results in a higher score. The score for a change is also depending on the topography of the position (e.g. changing an I-nternal side chain is/could be more dramatic/damageable for the entire structure than changing an E-xternal side chain) due to the different spatial constrains.

Thus, in one embodiment any method according to the current invention further comprises in the step of quantifying the difference of aligned framework positions in which the non-human heavy chain or light chain variable domain and the (first) humanized variant of said non-human heavy chain or light chain variable domain have different amino acid residues, which, due to the difference, influence antigen binding and/or three dimensional structure, by assigning a score to each difference of 0 (no influence on the conformation), 1 (slightly local influence), 2 (influence on the local conformation), 3 (strongly influence the local conformation and the neighboring strand or loop conformation), or 4 (will break the local conformation so severely that the antigen recognition will be disrupted).

A score of 0 is assigned to changes of surface located amino acid residues (in beta sheets or loops) as the side chains of 19 amino acid residues (all except proline) can be accommodated due to the free space present. An exception is proline: when the three-dimensional structure does not change the change is assigned a score of 0 otherwise, depending on the influence on antigen binding, the change is assigned a score of 3 or 4.

Thus, in one embodiment a score of 0 is assigned to a change of an amino acid residue with the topology E to any amino acid residue except proline (for which constrains as a cyclic residue are more important). Introduction of a proline has to be considered with regard to compatible Phi and Psi angles around this residue. For example, assuming that a polar residue in close proximity to CDR/HVR residues is replaced by a proline from the chosen germline, this replacement can be scored i) as 1 due to the change from a polar to hydrophobic residue, ii) as 2 or 3 depending on the angle compatibility, and iii) as 4 when angles and conformational changes for CDR/HVR residue(s) is(are) expected.

Internal amino acid residue changes are assigned a score depending on the free space available. The replacement with a smaller side chain will receive a low score, such as 0, and the replacement with a larger side chain will receive a score between 1 and 4 depending on the available space in the three-dimensional structure.

Thus, in one embodiment a score of 0 is assigned to a change of an amino acid residue with the topology I to an amino acid residue with a smaller side chain (i.e. for a conservative replacement), a score of 1 will be assigned to a change to an amino acid residue with a side chain that has one carbon atom more, a score of 2 will be assigned to a change to an amino acid residue with a side chain that has two carbon atoms more, a score of 3 will be assigned to a change an amino acid residue with a side chain that has three carbon atoms more, and a score of 4 will be assigned to all other changes.

Changes in antigen contacting amino acid residues will always be assigned a score of 4 when replaced.

Thus, in one embodiment a score of 4 is assigned to a change of an amino acid residue with the topology A to any other amino acid residue.

Amino acids that are not directly in contact with the antigen but are extremely close to amino acids designated as A are designated as L. Changes thereof lead sometimes to conformational changes that will be assigned a score of 3 or 4.

If an amino acid residue that is part of a pi-pi-/hydrophobic interaction is replaced by a non-hydrophobic amino acid residue the hydrophobic interaction is broken.

Such a replacement will be assigned a score of 3.

Thus, in one embodiment a score of 3 is assigned to the change of an amino acid residue with the topology C to a non-hydrophobic amino acid residue if thereby the interaction with an amino acid residue in the same domain or the corresponding variable domain is changed (reduced or eliminated).

If an amino acid residue that is part of a salt bridge is replaced by an oppositely charged or not-charged amino acid residue the salt bridge is broken. Such a replacement will be assigned a score of 3 in cases in which the salt bridge is solvent exposed and a score of 4 in cases in which the salt bridge is internal.

Thus, in one embodiment a score of 3 is assigned to a change of an amino acid residue with the topology S to an oppositely charged or not-charged amino acid residue in cases in which the salt bridge is solvent exposed and a score of 4 is assigned in cases in which the salt bridge is internal.

Some exemplary changes and the resulting score are shown in the following table.

| topology | change | score |
|---|---|---|
| L | G->Y | 4 |
| | T->K | 2 |
| | F->L | 2 |
| S | S->P | 2 |
| A | V->Y | 4 |
| | D->G | 4 |
| | T->N | 4 |
| I | V->W | 4 |
| | L->V | 2 |
| | L->I | 2 |
| | V->S | 3 |
| | V->A | 3 |
| | V->G | 3 |
| | L->F | 2 |
| | K->V | 2 |
| | V->L | 2 |
| | V->F | 3 |
| C | S->M | 2 |
| | F->A | 3 |
| | F->D | 3 |
| | L->R | 4 |
| | S->P | 2 |
| | Y->F | 2 |
| | H->Y | 3 |
| | H->D | 4 |
| | H->S | 4 |
| | T->Y | 4 |
| | T->K | 2 |
| | N->A | 2 |
| | N->P | 4 |
| | H->N | 3 |

The method as reported herein is in certain embodiments as follows:
  perform a sequence search by blending HVR1&2 of the V region (identify similar framework with known structure)
  do a separate sequence search for HVR3 (pick a HVR3 to graft on the selected framework)
  allow (very) small differences at the end of the J element (usually the J element from the structures chosen for the framework can be used as an acceptor template)
  establish a homology model (on the reconstructed model structure, mutate the deviating residues to reflect the original antibody sequence)
  determine the topology of the relevant residues
  establish a scoring matrix (from the alignment of the original non-human antibody sequence with the human germlines, all possible replacement with regard to the original antibody amino acid are scored)
  select acceptor germline(s) based on low cumulative scores (instead of overall percentage identity)
  decide based on the scoring matrix on the (back)mutations to be made.

The method as reported herein combines a three-dimensional assessment of the effect of changes with sequence information. In the method the non-human antibody is aligned with suitable human germline sequences. Using said alignment, the differences/required changes are quantified based on the topology in combination with the kind of change for each residue. The results are collected in a matrix.

The inventive method in general comprises the following steps:

The binding specificity of the non-human antibody is transferred onto a human or humanized acceptor framework to eliminate or at least reduce potential immunogenicity issues arising from non-human sequence stretches that the human body may recognize as foreign. This is done by engrafting the hypervariable regions (HVRs) of the non-human (donor) antibody onto a human/humanized (acceptor) antibody framework.

A suitable human (acceptor) antibody framework is identified in one case by aligning the non-human variable domain amino acid sequence to a collection of human germline antibody V-genes (germlines), and sorting them according to sequence identity and homology. The acceptor sequence is selected based on high overall sequence homology and optionally also the presence of the right canonical residues already in the acceptor sequence (see Poul, M-A. and Lefranc, M-P., in "Ingénierie des anticorps banques combinatores" ed. by Lefranc, M-P. and Lefranc, G., Les Editions INSERM, 1997). In addition, the conservation of the VH/VL angle can be taken into account.

The germline V-gene encodes only the region up to the beginning of CDR3 for the heavy chain, and till the middle of CDR3 of the light chain. Therefore, the genes of the germline V-genes are not aligned over the whole V-domain. The humanized construct comprises the human frameworks 1 to 3 and the non-human HVRs. The human framework 4 sequence is derived from a human JK-element or a human JH-element for light and heavy chain, respectively.

Before selecting one particular acceptor sequence, the so-called canonical loop structures of the donor antibody can be determined (see, e.g., Morea, V., et al., Methods, 20 (2000) 267-279). These canonical loop structures are determined by the type of residues present at so-called canonical positions. These positions lie (partially) outside of the HVRs and should be kept functionally equivalent in the final construct in order to retain the HVR conformation of the parental (donor) antibody.

In the following the invention is outlined with an antibody comprising the following heavy chain variable domain and light chain variable domain:

```
VH (122 amino acid residues) (SEQ ID NO: 01):
QIQLQESGPG LVKPSQSLSL TCSVTGFSIT TSGYYWTWIR

QFPGKKLEWM GYIGYNSKTY YNPSLKSRIS ITRDTSKNQF

LLHLNSVTTE DTATYYCARS LYGGYKDAFD SWGQGTLVTV

SS

VL (107 amino acid residues) (SEQ ID NO: 05):
DVVLTQTPAT LSAIPGERVT MTCKASQSIG TSLHWYQHRP

NETPRLLIKF ASRSITGIPS RFSGSGSGTD FTLGINNLEA

EDFAIYYCQQ SPGFPPTFGS GTKLEIN
```

With the amino acid sequence of the non-human antibody a model is build.

For the heavy chain the PDB is searched for a homolog to check if a very close homolog is present in the structure database for both framework regions and HVRs.

To identify suitable frameworks a search is made using only the V region and blending the HVRs (when underlined residues are also added then the HVR corresponds to the combined Kabat and Chothia CDRs):

```
QIQLQESGPG LVKPSQSLSL TCSVTGxxxx xxxxxxTWIR

QFPGKKLEWM xxxxxxxxxx xNPSLKSRIS ITRDTSKNQF

LLHLNSVTTE DTATYYCAR
```

The result is as follows.

|  | Score (bits) | E-Value |
|---|---|---|
| ↓JSAE structpro: 32C2 IGG1 ANTIBODY 32C2; CHA1N: . . . | 138 | 9e-34 |

```
structpro: 32CZB IGG1 ANTIBODY 32C2; CHAIN:
A; FRAGMENT: LIGHT CHAIN, VARIABLE REGION;
Length = 218

Score = 138 bits (348), Expect = 9e-34,
Identities = 70/98 (71%), Positives =
73/98 (74%), Gaps = 1/98 (1%)

VH      IQLQESGPGL VKPSQSLSLT CSVTGXXXXX XXXXXTWIRQ
        +QLQESGPGL VKPSQSLSLT C+VTG           WIRQ
PDB-1   VQLQESGPGL VKPSQSLSLT CTVTGYSISS DYAW-NWIRQ

VH      FPGKKLEWMX XXXXXXXXXX NPSLKSRISI TRDTSKNQFL
        FPG KLEWM             NPSLKSRISI TRDTSKNQF
PDB-1   FPGNKLEWMG YISYSGSTSY NPSLKSRISI TRDTSKNQFF

VH      LHLNSVTTED TATYYCAR
        L L+SVTTED TATYYCAR
PDB-1   LQLSSVTTED TATYYCAR
```

The alignment is checked to identify if there is some insertion or deletion and if there is a particular framework where the homology is particularly poor (in such cases it is possible to search for specific framework 1, 2, or 3 separately).

It has been found that the amino acid content within the HVR guides the conformation of the HVR.

By searching for a model for the non-human antibody it could be found that e.g. HVR-H1 is different in the model build on the structure found by blending the HVRs with regard to the X-ray structure. Now, then searching is done for every HVR loop separately. In this case, gaps are not allowed; if the short segment has a different length, it has then a different conformation.

```
HVR-H1:
TGFSITTSGYYWTW structpro: 3B2UF IMC-11F8 FAB LIGHT CHAIN;
CHAIN: L, D1 GI K, O, R, U, X; ENG1NEERED:
YES; Length = 215

Score = 32.7 bits (64), Expect = 0.058,
Identities = 10/18 (55%), Positives =
15/18 (83%)

Query:     1     SVTGFSITTSGYYWTWIR     18
                 +V+G SI++  YYW+WIR
Sbjct:    23     TVSGGSISSGDYYWSWIR     40

HVR-H2:
WMGYIGYNSKTYYNP
```

|  | Score (bits) | E-Value |
|---|---|---|
| ↓JSAE structpro: 2EKSB ANTI-LYSOZYME ANTIBODY FV . . . | 31 | 0.39 |
| ↓JSAE structpro: 32C2B IGG1 ANTIBODY 32C2; CHA1N: A . . . | 29 | 1.1 |
| ↓JSAE structpro: 1KCVH PC282 IMMUNOGLOBULIN; CHA1N: . . . | 29 | 1.1 |

-continued

```
HVR-H3:
YCARSLYGGYKDAFDSWG structpro: 1VGEH TR1.9 FAB; CHAIN: L;
FRAGMENTzFAB FRAGMENT OF A HUMAN IGG1 KAPPA
AUTOANTIBODY; ENGINEERED: YES; Length = 225

Score = 31.2 bits (69), Expect = 0.30,
Identities = 12/18 (66%), Positives = 12/18 (66%)

Query:     1    YCARSLYGGYKDAFDSWG     18
                YCAR  YGG K  FD WG
Sbjct:    96    YCARDPYGGGKSEFDYWG    113
```

Building a model for the heavy chain: The structure will be built by following the bold sequences. In this example: 32C2-FR1, 3B2U-HVR-H1, 32C2-FR2/HVR-H2/FR3, 1VGE-HVR-H3/J-element.

```
                                                      40
2eksb   QVQ.LQESGP GLMKPSETLS LTCSVSGDSI RSD..YWSWI
32c2b   DVQ.LQESGP GLVKPSQSLS LTCTVTGYSI SS.DYAWNWI
3b2uf   QVQ.LQESGP GLVKPSQTLS LTCTVSGGSI SSGDYYWSWI
VH      QIQ.LQESGP GLVKPSQSLS LTCSVTGFSI TTSGYYWTWI
1vgeh   QVKLLEQSGA EVKKPGASVK VSCKASGYSF TS..YGLHWV 80
2eksb   RQPPGKGLEW IGYVSY.SGS TYYNPSLKSR VTISVDTSKN
32c2b   RQFPGNKLEW MGYISY.SGS TSYNPSLKSR ISITRDTSKN
3b2uf   RQPPGKGLEW 1GYIYY.SGS TDYNPSLKSR VTMSVDTSKN
VH      RQPPGKKLEW MGYIGY.NSK TYYNPSLKSR ISITRDTSKN
1vgeh   RQAPGQRLEW MGWISAGTGN TKYSQKFRGR VTFTRDTSAT 120
2eksb   RFSLKLNSVT AADTAVYYCA RW........ DGDYWGQGIL
32c2b   QFFLQLSSVT TEDTATYYCA R.GYYGSSHS ..PVWGAGTT
3b2uf   QFSLKVNSVT AADTAVYYCA RVSIFG..VG TFDYWGQGTL
VH      QFLLHLNSVT TEDTATYYCA R.SLYGGYKD AFDSWGQGTL
1vgeh   TAYMGLSSLR PEDTAVYYCA R.DPYGGGKS EFDYWGQGTL 160
2eksb   VTVSS..... .......... .......... ..........
32c2b   VTVSSAKTTP PPVYPLVPGS LAQTNSMVTL GCLVKGYFPE
3b2uf   VTVSSASTKG PSVFPLAPS. .....GTAAL GCLVKDYFPE
VH      VTVSS..... .......... .......... ..........
1vgeh   VTVSSASTKG PSVFPLAPSS KSTSGGTAAL GCLVKDYFPE
```

The modeling can use the WolfGuy antibody numbering scheme that assigns a unique index to every position in the Fv, identifies CDR loop tips and discriminates between ascending and descending loop segments. The initial Wolf-Guy numbering of the input sequences, the equivalent of performing a sequence alignment with the available antibody template structures, forms the basis for template selection, VH-VL orientation adjustment and model refinement. Unlike other published antibody modeling protocols, framework templates are not selected per VH and VL or per Fv, but for every framework segment separately to minimize the number of necessary amino acid exchanges. After the raw model has been assembled from different template structures for framework and CDR regions, each residue is examined with regard to its (altered) chemical neighborhood formed by certain types of sidechains in its vicinity. Based on a conserved neighborhood definition for each position in the Fv, the sidechain (and to a certain extent also backbone) conformation of a given residue are adopted from matching known chemical neighborhood constellations.

Finally, the VH-VL orientation is adjusted based on first predicting the absolute parameters of VH-VL orientation from the amino acid types of certain key residues at the domain interface, followed by a coordinate transformation that applies the predicted orientation parameters to the model.

The same procedure is performed for the light chain variable domain.

When making a comparison between any two amino acid based structures, generally distance-based metrics such as the root-mean-square deviation (RMSD) of equivalent atoms are used.

To characterize the orientation between any two three-dimensional objects, it is necessary to define:
a frame of reference on each object,
axes to measure orientation parameters about,
terminology to describe and quantify these parameters.

The ABangle concept is a method which fully characterizes VH-VL orientation in a consistent and absolute sense using five angles (HL, HC1, LC1, HC2 and LC2) and a distance (de). The pair of variable domains of an antibody, VH and VL, is denoted collectively as an antibody Fv fragment.

The most structurally conserved residue positions in the heavy and light domains are used to define domain location. These positions are denoted as the VH and VL core-sets. These positions are predominantly located on the β-strands of the framework and form the core of each domain. The core-set positions are given in the following Table:

| light chain | heavy chain |
| --- | --- |
| L44 | H35 |
| L19 | H12 |
| L69 | H38 |
| L14 | H36 |
| L75 | H83 |
| L82 | H19 |
| L15 | H94 |
| L21 | H37 |
| L47 | H11 |
| L20 | H47 |
| L48 | H39 |
| L49 | H93 |
| L22 | H46 |
| L81 | H45 |
| L79 | H68 |
| L80 | H69 |
| L23 | H71 |
| L36 | H70 |
| L35 | H17 |
| L37 | H72 |
| L74 | H92 |
| L88 | H84 |
| L38 | H91 |
| L18 | H90 |
| L87 | H20 |
| L17 | H21 |
| L86 | H85 |
| L85 | H25 |
| L46 | H24 |
| L70 | H86 |
| L45 | H89 |
| L16 | H88 |
| L71 | H87 |
| L72 | H22 |
| L73 | H23 |

The core-set positions were used to register frames of reference onto the antibody Fv region domains.

The two reference frame planes are mapped onto any Fv structure. Therefore, the measuring of the VH-VL orientation can be made equivalent to measuring the orientation between the two planes. To do this fully and in an absolute sense requires at least six parameters: a distance, a torsion angle and four bend angles. These parameters must be measured about a consistently defined vector that connects the planes. This vector is denoted C in the following. To identify C, the reference frame planes were registered onto each of the structures in the non-redundant set as described above and a mesh placed on each plane. Each structure therefore had equivalent mesh points and thus equivalent VH-VL mesh point pairs. The Euclidean distance is measured for each pair of mesh points in each structure. The pair of points with the minimum variance in their separation distance is identified. The vector which joins these points is defined as C.

The coordinate system is fully defined using vectors, which lie in each plane and are centered on the points corresponding to C. H1 is the vector running parallel to the first principal component of the VH plane, while H2 runs parallel to the second principal component. L1 and L2 are similarly defined on the VL domain. The HL angle is a torsion angle between the two domains. The HC1 and LC1 bend angles are equivalent to tilting-like variations of one domain with respect to the other. The HC2 and LC2 bend angles describe twisting-like variations of one domain to the other.

The term "VH-VL orientation" is used in accordance with its common meaning in the art as it would be understood by a person skilled in the art (see, e.g., Dunbar et al., Prot. Eng. Des. Sel. 26 (2013) 611-620; and Bujotzek, A., et al., Proteins, Struct. Funct. Bioinf., 83 (2015) 681-695). It denotes how the VH and VL domains orientate with respect to one another.

Thus the VH-VL orientation is defined by
the length of C, dc,
the torsion angle, HL, from H1 to L1 measured about C,
the bend angle, HC1, between H1 and C,
the bend angle, HC2, between H2 and C,
the bend angle, LC1 between L1 and C, and
the bend angle, LC2, between L2 and C,
wherein reference frame planes are registered by i) aligning the Cα coordinates corresponding to the eight positions H36, H37, H38, H39, H89, H90, H91 and H92 of VH and fitting a plane through them, and ii) aligning the Cα coordinates corresponding to the eight positions L35, L36, L37, L38, L85, L86, L87 and L88 of VL and fitting a plane through them, iii) placing a placed on each plane, whereby each structure has equivalent mesh points and equivalent VH-VL mesh point pairs, and iv) measuring the Euclidean distance for each pair of mesh points in each structure, whereby the vector C joins the pair of points with the minimum variance in their separation distance, wherein H1 is the vector running parallel to the first principal component of the VH plane, H2 is the vector running parallel to the second principal component of the VH plane, L1 is the vector running parallel to the first principal component of the VL plane, L2 is the vector running parallel to the second principal component of the VL plane, the HL angle is the torsion angle between the two domains, the HC1 and LC1 are the bend angles equivalent to tilting-like variations of one domain with respect to the other, and the HC2 and LC2 bend angles are equivalent to the twisting-like variations of one domain to the other.

Thereafter an energy minimization of both chains together taking into account all side chains and their environment is performed using suitable software, e.g. the software INSIGHT from Accelrys.

The two or more structures that have delivered the frameworks, for the heavy chain and for the light chain, are superimposed using both variable domains taking into account the VH/VL angle.

The complex VH-VL is then energy minimized, e.g. using the module "discover" of Insight. The minimization process, e.g., follow the VA09A gradient for 600 cycles with a threshold derivative of 1 kcal/A; the partial charges are considered.

Establishment of the Scoring Matrix

For each amino acid position of the non-human antibody model structure the effect on the three-dimensional structure for every possible replacement considering a list of human germline sequences is quantified by assigning a score.

The quantification is done for each position and each replacement.

A topological description is assigned for each position based on the structure:
I: internal side chain
E: external side chain
C: contact H-L chains
A: antigen contact
L: linker to antigen
S: salt bridge Scores are assigned for each replacement as follow:
0: no influence of this replacement to the conformation
1: small local influence (local arrangement of some side chains)
2: influence on the local conformation
3: strong influence on the local conformation and the neighboring strand or loop conformation
4: will severely break the local conformation (can influence antigen binding)

How the scores are assigned is depending on the topography of the position and the change:
1. amino acid with external side chain on beta sheets or exposed loops: for a change in such a position, the assigned score is normally "0" because most of the 20 naturally occurring amino acid residues can be accommodated due to the free space present; proline or big residues like tryptophan have to be assigned on a case by case basis.
2. amino acid with internal side chain: the assigned score is depending on the free space available; replacement of linear through branched amino acids must be checked with effective replacement and eventually minimization (strong deviations are leading to high scores).
3. amino acid with antigen contacting side chain: when an amino acid is supposed to directly interact with the antigen, any replacement thereof is assigned a score of "4".
4. linker amino acid: those amino acids that are not directly in contact with the antigen but are extremely close to amino acids designated as "A"; strong differences for such amino acids can lead to conformational changes resulting in high scores of "3" or "4".
5. amino acid with contact side chain: such amino acids are located at the interface between light and heavy chains; are important for the stability of the complex; if a salt bridge is present, any replacement should allow this closed interaction to take place after replacement; similarly, hydrogen bonds are directional interactions; replacement of side chain leads usually to disruption of the directionality and have to be scored high ("3" or "4").
6. Salt bridges that are not (much) exposed to solvent are bringing a lot of interaction energy between the positive and the negative charges; breaking salt bridges may lead to a significant loss of stability within a domain or at the interface between the light and the heavy chain.

| structure position | comment |
|---|---|
| | The replacement by a similar amino acid is usually tolerated while completely changing the side chain characteristics effect as score different from "0". |
| E | When a side chain is exposed to the solvent, its replacement is usually not problematic; particular amino acids may be avoided: exposed tryptophan or methionine susceptible to oxidation; proline cyclization may change the conformation. |
| I | A protein structure has also internally some available space around an amino acid side chain; not all atoms of an internal amino acid side chain are in contact with neighboring amino acids; replacement is assigned a score based on the available free space. |
| C | Between the heavy and the light chain variable domain is no covalent linkage: therefore a score different from "0" will be assigned for each replacement that lowers the interaction energy between both variable domains; replacement that sterically influence the orientation of the domain will be assigned a score of "3" or "4" depending on the proximity to the HVRs. |
| A | "A" will be chosen for all side chains oriented toward a putative antigen in the surrounding of the antigen binding pocket; the amino acids "A" are supposed to be critical for antigen binding; replacement will always be assigned a score of "4". |
| L | Amino acids that are not supposed to interact directly with the antigen (not exposed but internal side chains) but are previous or subsequent to the amino acids designated as "A"; replacing them may strongly influence the close "A"s. |
| S | Salt bridges are bringing high interaction energies: breaking them affects the intrinsic stability of the antibody; usually, score of "1" or "2" will be assigned to reflect this loss; a higher score of "3" or "4" will be assigned if the linker is involved in a hydrophobic patch or makes several van der Waals contacts. |

The terms aromatic, linear or branched are describing the amino acid side chains. The terms polar, negative or positive are describing the functionality at the end of the side-chain.

| | amino acid (one letter code) | | | | |
|---|---|---|---|---|---|
| structure position | A small, hydrophobic | C linear, polar | D linear, negative | E linear, negative | G no side chain |
| E | | free cysteines are avoided | | | |
| I | 18 amino acids are bigger than alanine | breaking disulfide bridges is assigned a high score | change to hydrophobic residue is assigned a score | | all other amino acids are bigger than glycine |
| C | | n. a. | | | replacement results in assignment of score based on size of side chain |
| A | | n. a. | | | |
| L | | n. a. | | | |
| S | n. a. | n. a. | exchange of E/D sometimes possible; change to polar residues is assigned low score; change to hydrophobic or positive residue is assigned high score | | n. a. |

-continued

| | amino acid | | | |
|---|---|---|---|---|
| structure position | H aromatic, polar, neutral or charged (depending on pH and environment) | K linear, positive | R linear, positive | I branched, hydrophobic |
| E | | | | |
| I | | | | |
| C | | | | |
| A | | | | |
| L | | | | |
| S | | | exchange of K/R sometimes possible; change to polar residues is assigned low score; change to hydrophobic or positive residues is assigned high score | n. a. |

| | amino acid | | | | |
|---|---|---|---|---|---|
| structure position | L branched, hydrophobic | M linear | N linear, polar | P cyclic, hydrophobic | Q linear, polar |
| E | | | | replacing proline leads to less rigidity; turn induced by a proline needs to be conserved | |
| I | | | | | |
| C | | | | | |
| A | | | | replacement of proline in CDR/HVR will make the antibody more flexible | |
| L | | | | | |
| S | n. a. | n. a. | n. a. | n. a. | n. a. |

| | amino acid | | | | |
|---|---|---|---|---|---|
| structure position | S linear, polar | T branched (beta), polar | V branched (beta), hydrophobic | W double ring, aromatic | F aromatic, hydrophobic |
| E | | | | has the double ring particular interaction with neighbors? | has the phenyl ring particular interaction with neighbors? |
| I | | | | | |
| C | | | | | |
| A | | | | | |
| L | | | | | |
| S | n. a. | n. a. | n. a. | n. a. | n. a. |

| | amino acid Y hydrophobic aromatic with a polar function at the end | |
|---|---|---|
| structure position | | |
| E | has the phenyl ring particular interaction with neighbors? | insertion or deletion is normally scored with a "4" |
| I | | |
| C | | |
| A | | |
| L | | |
| S | n. a. | |

The assigned scores for each putative replacement at each position of the variable domain based on the available human germline sequences can be collected in a matrix.

For each position of an aligned sequence set (antibody in question—germlines) there are only a few residues that can actually be considered for a replacement, i.e. are occurring in this position in other/all germlines. The score is assigned
- by judging the relative importance based on the structural domain; and/or
- by executing the replacement on the model and quantifying a score regarding the grade of influence that this replacement induces; and/or
- by replacing and minimizing the overall structure: changing local conformation without affecting "A" residues or the stability of the complex can be scored with lower grade; displacing "A" side chains is severely sanctioned.

The scoring matrix resulting from the above outlined approach for part of this exemplary antibody (24 N-terminal residues of VH/SEQ ID NO: 01) is depicted in the following Table (Table discloses SEQ ID NO: 72).

| aa seq. | Q | I | Q | L | Q | E | S | . | G | P | G | L |
|---|---|---|---|---|---|---|---|---|---|---|---|---|
| topol. | E | I | E | I | E | I | E |   | E | E | E | E |
| A |   |   |   |   |   |   |   |   |   | 0 |   |   |
| C |   |   |   |   |   |   |   |   |   |   |   |   |
| D |   | 0 |   |   |   |   |   |   |   |   |   |   |
| E |   |   |   |   |   |   |   |   |   |   |   |   |
| F |   |   |   |   |   |   |   |   |   |   |   |   |
| G |   |   |   |   |   |   |   |   |   |   | 0 |   |
| H |   |   |   |   |   |   |   |   |   |   | 0 |   |
| I |   |   |   |   |   |   |   |   |   |   |   |   |
| K |   |   |   |   |   |   |   |   |   |   |   |   |
| L |   | 0 |   |   |   |   |   |   |   |   |   |   |
| M |   | 1 |   |   |   |   |   |   |   |   |   |   |
| N |   |   |   |   |   |   |   |   |   |   |   |   |
| P |   |   |   |   |   |   |   |   |   |   |   |   |
| Q |   |   |   |   |   | 1 |   |   |   |   |   |   |
| R |   |   |   |   |   |   |   |   | 2 |   |   |   |
| S |   |   |   |   |   |   |   |   |   |   | 0 |   |
| T |   |   |   | 0 |   | 0 |   |   |   |   |   |   |
| V |   | 0 |   |   |   |   |   |   |   |   |   |   |
| W |   |   |   |   |   |   | 1 |   |   |   |   |   |
| Y |   |   |   |   |   |   |   |   |   |   |   |   |

| aa seq. | V | K | P | S | Q | S | L | S | L | T | C | S | V |
|---|---|---|---|---|---|---|---|---|---|---|---|---|---|
| topol. | I | E | E | E | E | E | I | E | I | E | I | E | I |
| A |   |   |   |   |   |   |   |   |   |   |   |   |   |
| C |   |   |   |   |   |   |   |   |   |   |   |   |   |
| D |   |   |   |   |   |   |   |   |   |   |   |   |   |
| E |   |   |   |   |   |   |   |   |   |   |   |   |   |
| F |   |   |   |   |   |   |   |   |   |   |   |   |   |
| G |   |   | 0 |   |   |   |   |   |   |   |   |   |   |
| H |   |   |   |   |   |   |   |   |   |   |   |   |   |
| I | 0 |   |   |   |   |   |   |   |   |   |   |   |   |
| K | 1 |   |   |   |   |   |   |   |   |   |   |   |   |
| L | 0 |   |   |   |   |   |   |   |   |   |   |   |   |
| M |   |   |   |   |   |   |   |   |   |   |   |   |   |
| N |   |   |   |   |   |   |   |   |   |   |   |   |   |
| P |   |   |   |   |   |   |   |   |   |   |   | 2 |   |
| Q |   |   |   |   |   |   |   |   |   |   |   |   |   |
| R |   |   |   |   |   |   |   |   |   |   |   | 0 |   |
| S |   |   |   |   |   |   |   |   |   |   |   |   |   |
| T |   |   |   |   |   |   |   |   |   |   |   | 0 |   |
| V |   |   |   |   |   |   |   |   |   |   |   |   |   |
| W |   |   |   |   |   |   |   |   |   |   |   |   |   |
| Y |   |   |   |   |   |   |   |   |   |   |   |   |   |

Select Human Germline and Humanization

All scores are summed for a putative acceptor germline (without HVRs; forward mutations can also be considered). Human germlines are then sorted using the overall score. Selection of a germline framework to support humanization, which have an identical score, is based on the usage frequency of the particular framework; preference will be given to germlines that are occurring more often in humans. The scoring is separately done for the V region and the J element (separate scoring sums for every of the three frames can be done in an alternative and decide to make combination of them).

For a conservative humanization amino acid replacements with scores up to 2 are accepted and amino acid changes with scores of 3 or 4 are not accepted (these amino acid residues are not changed and kept as original); within HVRs all amino acids enclosed between 2 residues with a score of 4 are kept as original (not changed to human).

The definition of the HVRs is not fixed as defined by Chothia or Kabat: in some cases, the HVRs may be smaller than the above definition; on the other hand, HVRs can include some amino acids of the previous or subsequent framework.

For a less conservative humanization only amino acid changes with score of 4 are rejected and backmutated in the framework regions; within HVRs all amino acids enclosed between 2 residues with a score of 4 are kept as original (not changed to human).

For even less conservative humanizations replacement of amino acids between 2 "A" residues within HVRs that have a score lower than or equal to 2 can be done.

Example 1—Humanization of Murine Anti-IL-17 Antibody

Of a murine anti-IL17 antibody humanized variants have been generated using the method as reported herein with quantifying the influence on three-dimensional structure (scoring) of the different residues according to the scoring table reported herein.

For the heavy chain of SEQ ID NO: 09 a homology model has been generated according to the method as outlined above and a topography as shown has been assigned to each residue as shown in the following table (upper row: residue numbering according to Kabat; middle row: amino acid sequence; lower row: topography) (SEQ ID NO: 9 disclosed below).

| 1 | 2 | 3 | 4 | 5 | 6 | 7 | * | 8 | 9 | 10 | 11 | 12 | 13 | 14 | 15 | 16 | 17 | 18 |
|---|---|---|---|---|---|---|---|---|---|---|---|---|---|---|---|---|---|---|
| Q | V | Q | L | K | E | S | . | G | P | G | L | V | A | P | S | Q | S | L |
| E | I | E | I | E | I | E | . | E | E | E | E | S | E | E | E | S | E | I |

| 19 | 20 | 21 | 22 | 23 | 24 | 25 | 26 | * | 27 | 28 | 29 | 30 | 31 | 32 | 33 | 34 | 35 | 35a |
|---|---|---|---|---|---|---|---|---|---|---|---|---|---|---|---|---|---|---|
| S | I | T | C | T | V | S | G | . | F | S | L | D | S | . | . | . | . | . |
| E | I | E | I | E | I | E | E | . | I | L | L | L | A | . | . | . | . | . |

-continued

| 35b | * | * | * | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|
| Y | G | V | H | W | V | R | Q | P | P | G | K | G | L | E | W | L | V | V |
| L | L | I | C | I | C | S | C | E | E | E | E | C | C | S | C | I | I | A |

| 51 | 52 | 52a | 52b | 52c | * | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|
| I | W | S | . | . | . | . | D | G | T | T | T | Y | N | S | A | L | K | S |
| I | A | A | L | | | | A | A | A | L | C | E | C | S | S | I | S | E |

| 66 | 67 | 68 | 69 | 70 | 71 | 72 | 73 | 74 | 75 | 76 | 77 | 78 | 79 | 80 | 81 | 82 | 82a | 82b |
|---|---|---|---|---|---|---|---|---|---|---|---|---|---|---|---|---|---|---|
| R | L | S | I | T | K | D | N | S | K | S | Q | V | F | L | K | M | N | S |
| S | I | E | I | E | I | S | I | E | E | E | E | I | E | I | E | I | E | E |

| 82c | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|
| L | Q | T | D | D | T | A | I | Y | Y | C | A | R | D | T | H | Y | R | L |
| I | E | E | E | S | E | I | E | I | C | I | I | S | A | L | A | L | L | A |

| 100a | 100b | 100c | 100d | 100e | 100f | 100g | 100h | 100i | * | * | * | * | * | * | * | * | * |
|---|---|---|---|---|---|---|---|---|---|---|---|---|---|---|---|---|---|
| Y | Y | Y | A | M | . | . | . | . | | | | | | | | | |
| A | A | A | A | E | | | | | | | | | | | | | |

| * | * | * | 101 | 102 | 103 | 104 | 105 | 106 | 107 | 108 | 109 | 110 | 111 | 112 | 113 |
|---|---|---|---|---|---|---|---|---|---|---|---|---|---|---|---|
| . | . | . | D | Y | W | G | Q | G | T | S | V | T | V | S | S |
| | | | S | I | C | I | E | E | I | E | I | E | I | E | E |

Thereby 2 critical positions/stretches have been identified (bold letters in the Table above).

For the heavy chain variable domain 8 humanization proposal have been generated without using the scoring approach (HC-2a-h; murine germline fragment: SEQ ID NO: 10; HC-2a-HC-2h: SEQ ID NO: 11 to 18; mVH IL-17: SEQ ID NO: 64).

|  | 23 | 24 | 25 | 26 | 27 | 28 | 29 | 30 | 31 | 35b | * | * | * | 36 | 37 | 38 | 39 | 40 | 41 |
|---|---|---|---|---|---|---|---|---|---|---|---|---|---|---|---|---|---|---|---|
| murine germline | t | v | s | G | F | S | L | T | S | Y | G | V | H | w | v | r | q | p | p |
| mVH IL-17 | t | v | s | G | F | S | L | D | S | Y | G | V | H | w | v | r | q | p | p |
| variant HC-2a | a | a | s | G | F | S | L | D | S | Y | Y | M | S | w | v | r | q | a | p |
| variant HC-2b | a | a | s | G | F | S | L | D | S | Y | Y | M | S | w | v | r | q | a | p |
| variant HC-2c | a | a | s | G | F | S | L | D | S | Y | G | M | H | w | y | r | q | a | p |
| variant HC-2d | t | v | s | G | F | S | L | D | S | Y | Y | W | S | w | i | r | q | p | p |
| variant HC-2e | a | a | s | G | F | S | L | D | S | Y | G | V | H | w | v | r | q | a | p |
| variant HC-2f | a | a | s | G | F | S | L | D | S | Y | G | M | H | w | v | r | q | a | p |
| variant HC-2g | a | a | s | G | F | S | L | D | S | Y | G | V | H | w | v | r | q | a | t |
| variant HC-2h | a | a | s | G | F | T | F | S | S | Y | G | V | H | w | v | r | q | a | t |

|  | 54 | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|
| murine germline | D | G | S | T | N | Y | N | S | A | L | K | S | r | l | s | i | s | k |
| mVH IL-17 | D | G | T | T | T | Y | N | S | A | L | K | S | r | l | s | i | t | k |
| variant HC-2a | D | G | T | T | Y | Y | A | D | S | V | K | G | r | f | t | i | s | r |
| variant HC-2b | D | G | T | T | Y | Y | A | D | S | V | K | G | r | f | t | i | s | r |
| variant HC-2c | D | G | T | K | Y | Y | A | D | S | V | K | G | r | f | t | i | s | r |
| variant HC-2d | D | G | T | T | N | Y | N | P | S | L | K | S | r | v | t | i | s | v |
| variant HC-2e | D | G | T | T | T | Y | N | S | A | L | K | S | r | f | t | i | s | r |

-continued

| | | | | | | | | | | | | | | |
|---|---|---|---|---|---|---|---|---|---|---|---|---|---|---|
| variant HC-2f | G | T | N | K | Y | Y | A | D | S | V | K | G | r | f | t | i | s | r |
| variant HC-2g | D | G | T | T | T | Y | N | S | A | L | K | S | r | f | t | i | s | r |
| variant HC-2h | D | G | T | T | T | Y | P | G | S | V | K | G | r | f | t | i | s | r | uppercase letter: in HVR; lowercase letter: in FR

Five additional humanization proposal have been generated for the heavy chain variable domain using the scoring approach (HC-2i-m: SEQ ID NO: 19 to 23; respective germline fragments SEQ ID NO: 32 to 36; murine germline: SEQ ID NO: 10; mVH IL-17: SEQ ID NO: 64).

| | 23 | 24 | 25 | 26 | 27 | 28 | 29 | 30 | 31 | 35b | * | * | * | 36 | 37 | 38 | 39 | 40 | 41 |
|---|---|---|---|---|---|---|---|---|---|---|---|---|---|---|---|---|---|---|---|
| murine germline | t | v | s | G | F | S | L | T | S | Y | G | V | H | w | v | r | q | p | p |
| mVH IL-17 | t | v | s | G | F | S | L | D | S | Y | G | V | H | w | v | r | q | p | p |
| variant HC-2i | a | v | s | G | F | S | L | D | S | Y | G | V | H | w | v | r | q | a | p |
| human germline | a | a | s | G | F | T | V | S | S | N | Y | M | S | w | v | r | q | a | p |
| scoring | 0 | | | | | | | | | | | | | | | | | | 1 |
| variant HC-2j | t | v | s | G | F | S | L | D | S | Y | G | V | S | w | i | r | q | p | p |
| human germline | t | v | s | G | G | S | I | S | S | Y | Y | W | S | w | i | r | q | p | p |
| scoring | | | | | | | | | | | | | 4 | | 1 | | | | |
| variant HC-2k | a | v | s | G | F | S | L | D | S | Y | G | V | H | w | v | r | q | a | p |
| human germline | a | a | s | G | F | T | V | S | S | N | Y | M | S | w | v | r | q | a | p |
| scoring | 0 | | | | | | | | | | | | | | | | | | 1 |
| variant HC-2l | t | v | s | G | F | S | L | D | S | Y | G | V | S | w | i | r | q | p | p |
| human germline | t | v | s | G | G | S | V | S | S | Y | Y | W | S | w | i | r | q | p | p |
| scoring | | | | | | | | | | | | | 4 | | 1 | | | | |
| variant HC-2m | t | v | s | G | F | S | L | D | S | Y | G | M | H | w | v | r | q | a | p |
| human germline | t | v | s | G | F | S | L | S | N | M | G | V | S | w | i | r | q | p | p |
| scoring | | | | | | | | | | | | | 0 | | | | | | 1 |

| | 54 | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|
| murine germline | D | G | S | T | N | Y | N | S | A | L | K | S | r | l | s | i | s | k |
| mVH IL-17 | D | G | T | T | T | Y | N | S | A | L | K | S | r | l | s | i | t | k |
| variant HC-2i | D | G | T | T | T | Y | N | S | A | L | K | S | r | l | t | i | s | r |
| human germline | G | G | S | T | Y | Y | A | D | S | V | K | G | r | f | t | i | s | r |
| scoring | | | | | | | | | | | | | | | 0 | | 0 | 1 |
| variant HC-2j | D | G | T | T | N | Y | N | P | A | L | K | S | r | v | t | i | s | v |
| human germline | S | G | S | T | N | Y | N | P | S | L | K | S | r | v | t | i | s | v |
| scoring | | | | | 4 | | | 2 | | | | | | 1 | 0 | | 0 | 2 |
| variant HC-2k | D | G | T | T | T | Y | N | S | A | L | K | S | r | l | t | i | s | r |
| human germline | G | G | S | T | Y | Y | A | D | S | V | K | G | r | f | t | i | s | r |
| scoring | | | | | | | | | | | | | | | 0 | | 0 | 1 |
| variant HC-2l | D | G | T | T | N | Y | N | P | A | L | K | S | r | v | t | i | s | v |
| human germline | S | G | S | T | N | Y | N | P | S | L | K | S | r | v | t | i | s | v |
| scoring | | | | | 4 | | | | | | | | | | 0 | | | |
| variant HC-2m | D | G | T | K | S | Y | S | T | S | L | K | S | r | l | t | i | s | k |
| human germline | N | D | E | K | S | Y | S | T | S | L | K | S | r | l | t | i | s | k |
| scoring | | | | | 0 | | | | | | | | | | 0 | | | | uppercase letter: in HVR; lowercase letter: in FR

The 8 proposal obtained without the approach as reported herein have been analyzed retroactively also with the approach as reported herein. The combined results are shown in the following Table (respective germline fragments SEQ ID NO; 24 to 31; murine germline: SEQ ID NO: 10; mVH IL-17: SEQ ID NO: 64; variants HC-2a-m: SEQ ID NOS 11, 11, 13-15, 13, 17-20, 19-20 and 23).

| | 23 | 24 | 25 | 26 | 27 | 28 | 29 | 30 | 31 | 35b | * | * | * | 36 | 37 | 38 | 39 | 40 | 41 |
|---|---|---|---|---|---|---|---|---|---|---|---|---|---|---|---|---|---|---|---|
| murine germline | t | v | s | G | F | S | L | T | S | Y | G | V | H | w | v | r | q | p | p |
| mVH IL-17 | t | v | s | G | F | S | L | D | S | Y | G | V | H | w | v | r | q | p | p |
| variant HC-2a | a | a | s | G | F | S | L | D | S | Y | M | S | w | v | r | q | a | p |
| human germline | a | a | s | G | F | T | V | S | S | N | Y | M | S | w | v | r | q | a | p |
| scoring | 0 | 1 | | | | | | 4 | 0 | 4 | | | | | | | | 1 |

-continued

| | | | | | | | | | | | | | | | | | | | |
|---|---|---|---|---|---|---|---|---|---|---|---|---|---|---|---|---|---|---|---|
| variant HC-2b | a | a | s | G | F | S | L | D | S | Y | Y | M | S | w | v | r | q | a | p |
| human germline | a | a | s | G | F | T | V | S | S | N | Y | M | S | w | v | r | q | a | p |
| scoring | 0 | 1 | | | | | | | | 4 | 0 | 4 | | | | | | 1 | |
| variant HC-2c | a | a | s | G | F | S | L | D | S | Y | G | M | H | w | v | r | q | a | p |
| human germline | a | a | s | G | F | T | F | S | S | Y | G | M | H | w | v | r | q | a | p |
| scoring | 0 | 1 | | | | | | | | | | 0 | | | | | | 1 | |
| variant HC-2d | t | v | s | G | F | S | L | D | S | Y | Y | W | S | w | i | r | q | p | p |
| human germline | t | v | s | G | G | S | I | S | S | Y | Y | W | S | w | i | r | q | p | p |
| scoring | | | | | | | | | | 4 | 4 | 4 | | 1 | | | | | |
| variant HC-2e | a | a | s | G | F | S | L | D | S | Y | G | V | H | w | v | r | q | a | p |
| human germline | a | a | s | G | F | T | V | S | S | N | Y | M | S | w | v | r | q | a | p |
| scoring | 0 | 1 | | | | | | | | | | | | | | | | 1 | |
| variant HC-2f | a | a | s | G | F | S | L | D | S | Y | G | M | H | w | v | r | q | a | p |
| human germline | a | a | s | G | F | T | F | S | S | Y | G | M | H | w | v | r | q | a | p |
| scoring | 0 | 1 | | | | | | | | | | 0 | | | | | | 1 | |
| variant HC-2g | a | a | s | G | F | S | L | D | S | Y | G | V | H | w | v | r | q | a | t |
| human germline | a | a | s | G | F | T | F | S | S | Y | D | M | H | w | v | r | q | a | t |
| scoring | 0 | 1 | | | | | | | | | | | | | | | | 1 | 0 |
| variant HC-2h | a | a | s | G | F | T | F | S | S | Y | G | V | H | w | v | r | q | a | t |
| human germline | a | a | s | G | F | T | F | S | S | Y | D | M | H | w | v | r | q | a | t |
| scoring | 0 | 1 | | | 1 | 2 | 2 | | | | | | | | | | | 1 | 0 |
| variant HC-2i | a | v | s | G | F | S | L | D | S | Y | G | V | H | w | v | r | q | a | p |
| scoring | 0 | | | | | | | | | | | | | | | | | 1 | |
| variant HC-2j | t | v | s | G | F | S | L | D | S | Y | G | V | S | w | i | r | q | p | p |
| scoring | | | | | | | | | | | | | 4 | | 1 | | | | |
| variant HC-2k | a | v | s | G | F | S | L | D | S | Y | G | V | H | w | v | r | q | a | p |
| scoring | 0 | | | | | | | | | | | | | | | | | 1 | |
| variant HC-2l | t | v | s | G | F | S | L | D | S | Y | G | V | S | w | i | r | q | p | p |
| scoring | | | | | | | | | | | | | 4 | | 1 | | | | |
| variant HC-2m | t | v | s | G | F | S | L | D | S | Y | G | M | H | w | v | r | q | a | p |
| scoring | | | | | | | | | | | | 0 | | | | | | 1 | |

| | 54 | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|
| murine germline | D | G | S | T | T | Y | N | S | A | L | K | S | r | l | s | i | s | k |
| mVH IL-17 | D | G | T | T | T | Y | N | S | A | L | K | S | r | l | s | i | t | k |
| variant HC-2a | D | G | T | T | Y | Y | A | D | S | V | K | G | r | f | t | i | s | r |
| human germline | G | G | S | T | Y | Y | A | D | S | V | K | G | r | f | t | i | s | r |
| scoring | | | | 4 | | 2 | 1 | 1 | 2 | | 0 | | 2 | 0 | | 0 | | 1 |
| variant HC-2b | D | G | T | T | Y | Y | A | D | S | V | K | G | r | f | t | i | s | r |
| human germline | G | G | S | T | Y | Y | A | D | S | V | K | G | r | f | t | i | s | r |
| scoring | | | | 4 | | 2 | 1 | | 2 | | 0 | | 2 | 0 | | 0 | | 1 |
| variant HC-2c | D | G | T | K | Y | Y | A | D | S | V | K | G | r | f | t | i | s | r |
| human germline | G | S | N | K | Y | Y | A | D | S | V | K | G | r | f | t | i | s | r |
| scoring | | 2 | 4 | | 2 | 1 | | 2 | | | 0 | | 2 | 0 | | 0 | | 1 |
| variant HC-2d | D | G | T | T | N | Y | N | P | S | L | K | S | r | v | t | i | s | v |
| human germline | S | G | S | T | N | Y | N | P | S | L | K | S | r | v | t | i | s | v |
| scoring | | | 4 | | | | | 2 | 1 | | | | 1 | 0 | | 0 | | 2 |
| variant HC-2e | D | G | T | T | T | Y | N | S | A | L | K | S | r | f | t | i | s | r |
| human germline | G | G | S | T | Y | Y | A | D | S | V | K | G | r | f | t | i | s | r |
| scoring | | | | | | | | | | | | | 2 | 0 | | 0 | | 1 |
| variant HC-2f | G | T | N | K | Y | Y | A | D | S | V | K | G | r | f | t | i | s | r |
| human germline | G | S | N | K | Y | Y | A | D | S | V | K | G | r | f | t | i | s | r |
| scoring | 4 | 4 | 2 | 4 | | 2 | 1 | | 2 | | 0 | | 2 | 0 | | 0 | | 1 |
| variant HC-2g | D | G | T | T | T | Y | N | S | A | L | K | S | r | f | t | i | s | r |
| human germline | A | G | D | T | Y | Y | P | G | S | V | K | G | r | f | t | i | s | r |
| scoring | | | | | | | | | | | | | 2 | 0 | | 0 | | 1 |
| variant HC-2h | D | G | T | T | T | Y | P | G | S | V | K | G | r | f | t | i | s | r |
| human germline | A | G | D | T | Y | Y | P | G | S | V | K | G | r | f | t | i | s | r |
| scoring | | | | | 4 | 1 | 1 | 2 | | 2 | | | 2 | 0 | | 0 | | 1 |
| variant HC-2i | D | G | T | T | T | Y | N | S | A | L | K | S | r | l | t | i | s | r |
| scoring | | | | | | | | | | | | | | 0 | | 0 | | 1 |
| variant HC-2j | D | G | T | T | N | Y | N | P | A | L | K | S | r | v | t | i | s | v |
| scoring | | | | | 4 | | 2 | | | | | | 1 | 0 | | 0 | | 2 |
| variant HC-2k | D | G | T | T | T | Y | N | S | A | L | K | S | r | l | t | i | s | r |
| scoring | | | | | | | | | | | | | | 0 | | 0 | | 1 |
| variant HC-2l | D | G | T | T | N | Y | N | P | A | L | K | S | r | v | t | i | s | v |
| scoring | | | | | 4 | | 2 | | | | | | 1 | 0 | | 0 | | 2 |
| variant HC-2m | D | G | T | K | S | Y | S | T | S | L | K | S | r | l | t | i | s | k |
| scoring | | | | 2 | 2 | | 1 | 1 | 1 | | | | | 0 | | 0 | | | uppercase letter: in HVR; lowercase letter: in FR

Out of the 13 humanization proposals 3 showed acceptable binding affinity. Two thereof were obtained without the approach as reported herein (2 of 8=25%), one was obtained with the method as reported herein (1 of 5=20%).

For the light chain variable domain 4 humanization proposal have been generated without using the scoring approach (LC-2a-d; SEQ ID NO: 37 to 40; murine germline: SEQ ID NO: 81; mVH IL-17: SEQ ID NO: 82).

|  | 24 | 25 | 26 | 27 | 27a | 27b | 27c | 27d | 27e | 27f | 28 | 29 | 30 | 32 | 33 | 34 | 35 | 36 | 37 | 38 | 39 |
|---|---|---|---|---|---|---|---|---|---|---|---|---|---|---|---|---|---|---|---|---|---|
| murine germline | R | S | S | Q | S | L | V | H | S | N | G | N | T | Y | L | H | w | y | l | q | k |
| mVH IL-17 | R | S | S | Q | S | L | V | H | S | N | G | D | T | Y | F | H | w | y | l | q | k |
| variant LC-2a | R | S | S | Q | S | L | V | H | S | N | G | D | T | Y | L | N | w | y | l | q | k |
| variant LC-2b | R | S | S | Q | S | L | V | H | S | N | G | D | T | Y | L | D | w | y | l | q | k |
| variant LC-2c | K | S | S | Q | S | L | V | H | S | N | G | D | T | Y | L | Y | w | y | l | q | k |
| variant LC-2d | R | S | S | Q | S | L | V | H | S | N | G | D | T | Y | F | H | w | y | l | q | k |

|  | 40 | 41 | 42 | 43 | 44 | 45 | 46 | 47 | 48 | 49 | 50 | 51 | 52 | 53 | 54 | 55 | 56 | 57 | 58 |
|---|---|---|---|---|---|---|---|---|---|---|---|---|---|---|---|---|---|---|---|
| murine germline | p | g | q | s | p | k | l | l | i | y | K | V | S | N | R | F | S | g | v |
| mVH IL-17 | p | g | q | s | p | k | l | l | i | y | K | V | S | N | R | F | S | g | v |
| variant LC-2a | p | g | q | s | p | r | r | l | i | y | K | V | S | N | R | D | S | g | v |
| variant LC-2b | p | g | q | s | p | q | l | l | i | y | K | V | S | N | R | A | S | g | v |
| variant LC-2c | p | g | q | p | p | q | l | l | i | y | K | V | S | N | R | F | S | g | v |
| variant LC-2d | p | g | q | s | p | q | l | l | i | y | K | V | S | N | R | F | S | g | v | uppercase letter: in HVR; lowercase letter: in FR

For the light chain of SEQ ID NO: 49 a homology model has been generated according to the method as outlined above and a topography as shown has been assigned to each residue as shown in the following table (upper row: residue numbering according to Kabat; middle row: topography; lower row: amino acid sequence) (residues 1-108 of SEQ ID NO: 49 disclosed below).

| 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|
| E | I | E | I | E | I | E | E | E | E | I | E | I | E | E | E | E | E |
| D | V | V | M | T | Q | T | P | L | S | L | P | V | S | L | G | D | Q |

| 19 | 20 | 21 | 22 | 23 | 24 | 25 | 26 | 27 | * | * | 27a | 27b | 27c | 27d | 27e | 27f | 28 |
|---|---|---|---|---|---|---|---|---|---|---|---|---|---|---|---|---|---|
| I | E | I | E | I | E | L | A | A |  |  | A | A | L | L |  |  |  |
| A | S | I | S | C | R | S | S | Q | . | . | S | L | V | H | S | N | G |

| 29 | 30 | 31 | 32 | 33 | 34 | 35 | 36 | 37 | 38 | 39 | 40 | 41 | 42 | 43 | 44 | 45 | 46 |
|---|---|---|---|---|---|---|---|---|---|---|---|---|---|---|---|---|---|
|  |  | L | L | C | I | C | I | C | I | C | C | C | E | C | C | E | C |
| D | T | . | Y | F | H | W | Y | L | Q | K | P | G | Q | S | P | K | L |

| 47 | 48 | 49 | 50 | * | * | * | * | * | * | * | 51 | 52 | 53 | 54 | 55 | 56 |
|---|---|---|---|---|---|---|---|---|---|---|---|---|---|---|---|---|
| I | I | C | L |  |  |  |  |  |  |  | A | A | L | E | C | E |
| L | I | Y | K | . | . | . | . | . | . | . | V | S | N | R | F | S |

| 57 | 58 | 59 | 60 | 61 | 62 | 63 | 64 | 65 | 66 | 67 | 68 | * | * | 69 | 70 | 71 | 72 |
|---|---|---|---|---|---|---|---|---|---|---|---|---|---|---|---|---|---|
| E | I | E | E | S | I | E | I | E | I | E | E |  |  | E | E | I | E |
| G | V | P | D | R | F | S | G | S | G | S | G | . | . | T | D | F | T |

| 73 | 74 | 75 | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|---|---|
| I | E | I | E | E | I | E | E | E | S | E | I | C | I | C | I | C | C |
| L | K | I | N | R | V | E | A | E | D | L | G | V | Y | F | C | S | Q |

| 91 | 92 | 93 | 94 | 95 | 95a | 95b | 95c | 95d | 95e | 95f | * | * | * | * | * | * |
|---|---|---|---|---|---|---|---|---|---|---|---|---|---|---|---|---|
| L | A | A | A | A |  |  |  |  |  |  |  |  |  |  |  |  |
| T | T | H | A | P | . | . | . | . | . | . | . | . | . | . | . | . |

| * | * | * | * | * | * | * | * | * | * | 96 | 97 | 98 | 99 | 100 | 101 | 102 | 103 |
|---|---|---|---|---|---|---|---|---|---|---|---|---|---|---|---|---|---|
|  |  |  |  |  |  |  |  |  |  | L | I | C | I | C | E | I | E |
| . | . | . | . | . | . | . | . | . | . | F | T | F | G | S | G | T | K |

Two additional humanization proposal have been generated for the light chain variable domain using the approach (LC-2e-f; SEQ ID NO: 41 and 42; respective germline fragments SEQ ID NO: 47 and 48; murine germline: SEQ ID NO:81 mVH IL-17: SEQ ID NO: 82).

| | 24 | 25 | 26 | 27 | 27a | 27b | 27c | 27d | 27e | 27f | 28 | 29 | 30 | 32 | 33 | 34 | 35 | 36 | 37 | 38 | 39 |
|---|---|---|---|---|---|---|---|---|---|---|---|---|---|---|---|---|---|---|---|---|---|
| murine germline | R | S | S | Q | S | L | V | H | S | N | G | N | T | Y | L | H | w | y | l | q | k |
| mVL IL-17 | R | S | S | Q | S | L | V | H | S | N | G | D | T | Y | F | H | w | y | l | q | k |
| variant LC-2e | R | S | S | Q | S | L | V | H | S | N | G | D | T | Y | F | H | w | y | l | q | k |
| human germline scoring | K | S | S | Q | S | L | L | H | S | D | G | K | T | Y | L | Y | w | y | l | q | k |
| variant LC-2f | R | S | S | Q | S | L | V | H | S | N | G | D | T | Y | F | H | w | y | l | q | k |
| human germline scoring | R | S | S | Q | S | L | V | Y | S | D | G | N | T | Y | L | N | w | f | q | q | r |

| | 40 | 41 | 42 | 43 | 44 | 45 | 46 | 47 | 48 | 49 | 50 | 51 | 52 | 53 | 54 | 55 | 56 | 57 | 58 |
|---|---|---|---|---|---|---|---|---|---|---|---|---|---|---|---|---|---|---|---|
| murine germline | p | g | q | s | p | k | l | l | i | y | K | V | S | N | R | F | S | g | v |
| mVL IL-17 | p | g | q | s | p | k | l | l | i | y | K | V | S | N | R | F | S | g | v |
| variant LC-2e | p | g | q | s | p | q | l | l | i | y | K | V | S | N | R | F | S | g | v |
| human germline scoring | p | g | q | p | p | q 0 | l | l | i | y | E | V | S | N | R | F | S | g | v |
| variant LC-2f | p | g | q | s | p | q | l | l | i | y | K | V | S | N | R | F | S | g | v |
| human germline scoring | p | g | q | s | p | r 0 | r | l | i | y | K | V | S | N | R | D | S | g | v | uppercase letter: in HVR; lowercase letter: in FR

The 4 proposal obtained without the approach as reported herein have been analyzed retroactively also with the approach as reported herein. The combined results are shown in the following Table (respective germline fragments SEQ ID NO: 43 to 46; murine germline: SEQ ID NO: 81; mVH IL-17: SEQ ID NO: 82; variants LC-2a-f: SEQ ID NOS 37-40, 40 and 40).

| | 24 | 25 | 26 | 27 | 27a | 27b | 27c | 27d | 27e | 27f | 28 | 29 | 30 | 32 | 33 | 34 | 35 | 36 | 37 | 38 | 39 |
|---|---|---|---|---|---|---|---|---|---|---|---|---|---|---|---|---|---|---|---|---|---|
| murine germline | R | S | S | Q | S | L | V | H | S | N | G | N | T | Y | L | H | w | y | l | q | k |
| mVL IL-17 | R | S | S | Q | S | L | V | H | S | N | G | D | T | Y | F | H | w | y | l | q | k |
| variant LC-2a | R | S | S | Q | S | L | V | H | S | N | G | D | T | Y | L | N | w | y | l | q | k |
| human germline scoring | R | S | S | Q | S | L | V | Y | S | D | G | N | T | Y | L | N | w | f | q | q | r |
| | | | | | | | | | | | | | | | 2 | 3 | | 2 | 0 | | 0 |
| variant LC-2b | R | S | S | Q | S | L | V | H | S | N | G | D | T | Y | L | D | w | y | l | q | k |
| human germline scoring | R | S | S | Q | S | L | L | H | S | N | G | Y | N | Y | L | D | w | y | l | q | k |
| | | | | | | | | | | | | | | | 2 | 4 | | | | | |
| variant LC-2c | K | S | S | Q | S | L | V | H | S | N | G | D | T | Y | L | Y | w | y | l | q | k |
| human germline scoring | K | S | S | Q | S | L | L | H | S | D | G | K | T | Y | L | Y | w | y | l | q | k |
| | | | | | | | | | | | | | | | 2 | 3 | | | | | |
| variant LC-2d | R | S | S | Q | S | L | V | H | S | N | G | D | T | Y | F | H | w | y | l | q | k |
| human germline scoring | R | S | S | Q | S | L | L | H | S | N | G | Y | N | Y | L | D | w | y | l | q | k |
| variant LC-2e | R | S | S | Q | S | L | V | H | S | N | G | D | T | Y | F | H | w | y | l | q | k |
| scoring | | | | | | | | | | | | | | | | | | | | | |
| variant LC-2f | R | S | S | Q | S | L | V | H | S | N | G | D | T | Y | F | H | w | y | l | q | k |
| scoring uppercase | | | | | | | | | | | | | | | | | | | | | |

| | 40 | 41 | 42 | 43 | 44 | 45 | 46 | 47 | 48 | 49 | 50 | 51 | 52 | 53 | 54 | 55 | 56 | 57 | 58 |
|---|---|---|---|---|---|---|---|---|---|---|---|---|---|---|---|---|---|---|---|
| murine germline | p | g | q | s | p | k | l | l | i | y | K | V | S | N | R | F | S | g | v |
| mVL IL-17 | p | g | q | s | p | k | l | l | i | y | K | V | S | N | R | F | S | g | v |
| variant LC-2a | p | g | q | s | p | r | r | l | i | y | K | V | S | N | R | D | S | g | v |
| human germline scoring | p | g | q | s | p | r 0 | r 4 | l | i | y | K | V | S | N | R | D 3 | S | g | v |
| variant LC-2b | p | g | q | s | p | q | l | l | i | y | K | V | S | N | R | A | S | g | v |
| human germline scoring | p | g | q | s | p | q 0 | l | l | i | y | L | G | S | N | R | A 3 | S | g | v |
| variant LC-2c | p | g | q | p | p | q | l | l | i | y | K | V | S | N | R | F | S | g | v |
| human germline scoring | p | g | q | p 2 | p | q 0 | l | l | i | y | E | V | S | N | R | F | S | g | v |
| variant LC-2d | p | g | q | s | p | q | l | l | i | y | K | V | S | N | R | F | S | g | v |
| human germline scoring | p | g | q | s | p | q 0 | l | l | i | y | L | G | S | N | R | A | S | g | v |

| | | | | | | | | | | | | | | | | | |
|---|---|---|---|---|---|---|---|---|---|---|---|---|---|---|---|---|---|
| variant LC-2e scoring | p | g | q | s | p | q 0 | l | l | i | y | K | V | S | N | R | F | S | g | v |
| variant LC-2f scoring | p | g | q | s | p | q 0 | l | l | i | y | K | V | S | N | R | F | S | g | v | uppercase letter: in HVR; lowercase letter: in FR

Out of the 6 humanization proposals only 4 showed acceptable binding affinity. Two thereof were obtained without the approach as reported herein (2 of 4=50%), two were obtained with the method as reported herein (2 of 2=100%).

Using the approach as reported herein it has been identified in the light chain variable domain that two residues, i.e. H34 and F55, are strongly influencing antigen binding.

The results for the respective humanized anti-IL17 antibodies are summarized in the following Table.

| HC | LC | Neutralization in NHDF | | BIAcore | |
|---|---|---|---|---|---|
| | | hIL-17A ELISA | IL-6 IC$_{50}$ (nM) | t/2$_{diss}$ (min) | K$_D$ (nM) |
| murine | murine | +++ | 0.21 | >1160 | 0.05 |
| chimeric | chimeric | 166 | 0.14 | 464 | 0.03 |
| HC2-e | LC2-a | 52 | 53.7 | 22 | 1.27 |
| HC2-e | LC2-d | 93 | 0.32, 0.05 | 206 | 0.07 |
| HC2-g | LC2-c | 118 | 2.3, 1.5 | 219 | 0.11 |
| HC2-g | LC2-d | 160 | 0.20, 0.01 | 230 | 0.07 |
| HC2-i | LC2-e | 181 | 0.33 | 174 | 0.09 |
| HC2-i | LC2-f | 175 | 1.1 | 139 | 0.11 |
| HC2-k | LC2-e | 175 | 0.52, 0.34 | 237 | 0.06 |
| HC2-m | LC2-e | 169 | 5.9 | 38 | 0.39 |
| HC2-m | LC2-f | 209 | 30.8 | 26 | 0.53 |

Thus, the number of inactive variants can be reduced by using the method according to the invention.

Example 2—Anti-CCR5 Antibody

Seventeen humanized variants of a murine anti-CCR5 antibody heavy chain variable domain have been generated using a conventional humanization method, i.e. without using the approach as reported herein. The binding to CCR5 has been determined for these variants. It can be seen that by using the method according to the invention it is possible to identify humanized variants that are unlikely to bind the antigen based on the total score and the number of amino acid differences, which are assigned a score of 4. Thereby antigen-binding inactive variants can be identified and deselected.

| VH variant | binding to CCR5 | total score | number of score "4" |
|---|---|---|---|
| murine VH | | 0 | |
| 15 | y | 3 | |
| 16 | y | 3 | |
| 18 | y | 3 | |
| 14 | y | 4 | |
| 17 | y | 6 | |
| 7 | n | 11 | 1 |
| 8 | n | 6 | 1 |
| 9 | n | 6 | 1 |
| 10 | y | 10 | 2 |
| 11 | y | 10 | 2 |
| 12 | y | 10 | 2 |
| 13 | y | 13 | 3 |
| 6 | n | 16 | 3 |
| 2 | n | 20 | 4 |
| 3 | n | 20 | 4 |
| 4 | n | 20 | 4 |
| 5 | n | 20 | 4 |

In certain methods and embodiments of this invention, a humanized antibody is made comprising amino acid sequence of a non-human antibody and a human germline sequence, utilizing the steps of:
a) obtaining the amino acid sequences of a non-human antibody variable domain and of i) a human germline sequence with the highest sequence homology to the non-human variable domain, or ii) two or more human germline sequence fragments that when aligned have a homology higher than a single human germline sequence, or iii) based on the VH/VL angle;
b) identifying hypervariable region amino acid sequences in the non-human antibody variable domain and the human germline sequences:
c) substituting a non-human antibody hypervariable region amino acid sequence for the corresponding human germline hypervariable region amino acid sequence;
d) aligning the amino acid sequences of a framework region (FR) of the non-human antibody and the corresponding FR of the human germline sequence;
e) identifying non-human antibody FR residues in the aligned FR sequences that are non-identical to the corresponding human germline residues;
f) determining if the non-identical non-human variable domain amino acid residue is reasonably expected to have at least one of the following topologies:
   I: internal side chain
   E: external side chain
   C: contact H-L chains
   A: antigen contact
   L: linker to antigen
   S: salt bridge
   and if the difference results in a score different from 0 determining for each amino acid residue at the respective position that is present at said position in any not selected human germline sequence the respective score and thereby generating a scoring matrix;
g) for any non-identical non-human antibody amino acid residue, which is reasonably expected to have at least one of these topologies, substituting that residue for the corresponding amino acid residue from the matrix that has the lowest score.

Optionally, it is determined if any non-identical residues identified in step (e) are exposed on the surface of the domain or buried within it, and if the residue is exposed but has none of the topologies identified in step (f), one may retain the human germline residue.

In one embodiment the method further comprises aligning non-human antibody and the human germline FR sequences, identifying non-human antibody FR residues which are non-identical with the aligned human germline FR sequence, and for each such non-identical non-human antibody FR residue, determining if the corresponding human germline residue represents a residue which is highly conserved across all species at that site, and if it is so conserved, preparing a humanized antibody which comprises the human germline amino acid residue at that site.

In one embodiment in the homology model the root mean square difference (RMSD) of the main chain conformations of the non-human antibody sequence and the template sequence is less than 4 Å, less than 3 Å, and preferably less than 2 Å.

In certain methods and embodiments of this invention, it is provided a method for the production of a humanized antibody, comprising at least one light chain and one heavy chain, the method comprising the steps of:
a) selecting a non-human antibody having at least one HVR;
b) selecting a human antibody heavy chain or germline sequence;
c) selecting a human antibody light chain or germline sequence
d) introducing at least one HVR from the non-human antibody heavy chain into the human antibody heavy chain, to form a recombinant heavy chain; and
e) introducing at least one HVR from the non-human antibody light chain into the human antibody light chain, to form a recombinant light chain;
f) changing amino acid residues in both variable domain amino acid sequences based on the method as reported herein,
wherein the selection of each of the human antibody heavy and light chains is determined solely by sequence homology with the non-human antibody heavy and light chains, respectively.

In certain methods and embodiments of this invention, it is provided a method of producing a humanized antibody comprising:
comparing the variable (V) region framework (FR) sequences of a non-human antibody to the variable (V) region framework (FR) sequences of human antibodies or human antibody germline sequences to determine the degree of sequence homology between the non-human antibody FRs and the human antibody or human germline FRs; and
replacing FRs in the non-human antibody with the human antibody or human germline FRs determined with the method as reported herein.

In one embodiment the assigning of a score comprises all changes as outlined herein.

In one embodiment the assigning of a score further comprises assigning a score of 0, 1, 2, 3, or 4 to each difference whereby
a change of a residue in the HVR of topology A is assigned a score of 4,
a change of a residue of the topology L, which has also the topology S, is assigned a score of 3 or 4 (with 4 being preferred),
a change of a residue of the topology C, which has a short side chain, to an amino acid residue with a smaller amino acid (based on volume) is assigned a score of at most 2,
a change of a residue of the topology C, which has a short side chain, to an amino acid residue with a bigger (volumetric) side chain is assigned a score of 2 or 3 depending on the size of the side chain and of the nature of the contact with the neighbored variable domain,
a change of a residue of the topology C, which has a short side chain, to an amino acid residue with a side chain that results in a change of the VH-VL orientation is assigned a score of 4,
a change of a residue of the topology C that has also the topology S is assigned a score of 4,
a change of a residue of topology S that has also the topology I is assigned a score of 4 or 3, respectively, for side chains of inverted charge and for neutral smaller side chains that only lack the appropriate charge,
a change of a residue of topology S, which has also the topology I, to an amino acid residue with a neutral but bigger side chain is assigned a score of 4,
a change of a residue of topology S, which has also the topology E, is assigned a score of 3 or 2, respectively, for side chains of inverted charge and for any side chain that only lack the appropriate charge,
a score of 0 is always assigned to changes of a residue of the topology S except for a change to proline, which is assigned a score of 0 when the three-dimensional structure is not changed and a score of at least 3 when the three-dimensional structure is changed,
a score of 0 is assigned to a change of an amino acid residue with the topology E to any amino acid residue except proline,
a change of an amino acid residue with the topology E to proline is assigned a score of 1 if the change is from a polar to hydrophobic residue, a score of 2 or 3 depending on the VH/VL-angle change, and a score of 4 when angles and conformational changes for HVR residue(s) is(are) expected,
a score of 0 is assigned to a change of an amino acid residue with the topology I to an amino acid residue with a smaller side, a score of 1 is assigned to a change to an amino acid residue with a side chain that has one carbon atom more, a score of 2 is assigned to a change to an amino acid residue with a side chain that has two carbon atoms more, a score of 3 is assigned to a change an amino acid residue with a side chain that has three carbon atoms more, and a score of 4 is assigned to all other changes,
a score of at least 3 is assigned to a change of an amino acid residue with the topology L when the change results in a conformational change,
a score of 3 is assigned to the change of an amino acid residue with the topology C to a non-hydrophobic amino acid residue if thereby the interaction with an amino acid residue in the same domain or the corresponding variable domain is changed,
a score of 3 or 4 is assigned to the change of an amino acid residue of the topology S when the residue is replaced by an oppositely charged or not-charged amino acid residue and the salt bridge is broken, whereby a score of 3 is assigned in cases in which the salt bridge is solvent exposed and a score of 4 is assigned in cases in which the salt bridge is internal,
a change to proline is assigned a score of 3 or 4 if the proline replacement changes the phi and psi angles around this residue, if a change to proline is not changing the conformation of the amino acid stretch around the residue it is assigned a score of 0 or 1,
a score of 4 is assigned to a change of an amino acid residue with the topology A to any amino acid residue, a score of 3 or 4 is assigned to the change of an amino acid residue with the topology C to a non-hydrophobic amino acid residue, whereby a score of 0 denotes no influence on framework stability or HVR conformation, a score of 1 denotes slight influence on framework stability or HVR conformation, a score of 2 denotes moderate influence on framework stability or HVR conformation, a score of 3 denotes that the change will affect framework stability, and a score of 4 denotes that the change will break framework stability or HVR conformation.

In one embodiment amino acid residues with a score of 4 are changed/mutated each to an amino acid residue resulting in a lower score or to amino acid residues resulting in a lower total score (=sum of all scores 3 and 4, optionally including scores of 2).

In one embodiment amino acid residues with a score of 4 and 3 are changed/mutated each to an amino acid residue resulting in a lower score or to amino acid residues resulting in a lower total score (=sum of all scores 3 and 4, optionally including scores of 2).

The following examples are provided to aid the understanding of the present invention, the true scope of which is set forth in the appended claims. It is understood that modifications can be made in the procedures set forth without departing from the spirit of the invention.

EXAMPLES

Example 1

Binding to IL-17 Measured by ELISA

NUNC® MaxiSorp plates (96-well) were coated with recombinant human IL-17 (Peprotech #200-17, www.peprotech.com) at a concentration of 0.5 µg/ml in PBS (100 ml/well). Plates were incubated at 37° C. on an orbital shaker with agitation for 2 hours. Thereafter coating solution was removed and 100 µl/well PBSTC (phosphate buffered saline, 0.05% Tween®-20, 2% chicken serum) was added. Plates were incubated at room temperature for 1 hour. Blocking solution was removed and samples (blank: PBSTC, samples (10 µg/ml in PBS)) were added to the plate (100 µl/well). Plates were incubated at room temperature with agitation. Samples were removed, plates were washed three times with 200 µl/well PBST (phosphate buffered saline, 0.05% Tween®-20) and secondary antibody (goat anti-human IgG, Fc gamma, HRP conjugate (Chemicon API 13P) for the detection of humanized antibodies was added. The second antibody was diluted 1:10,000 in PBSTC and plates were incubated for 1 hour at room temperature with agitation. Second antibody was removed, plates were washed three times with 200 µl/well PBST (phosphate buffered saline, 0.05% Tween®-20) and 100 µl/well ABTS® (Roche Diagnostics GmbH, Mannheim, Germany) was added. Optical density was measured at 405/492 nm.

Example 2

Preparation of an Expression Plasmid for an Immunoglobulin of Class IgG1

Plasmid p6454 was the expression plasmid for the expression of an anti-IL-17-antibody (genomically organized expression cassette with retained exon-intron organization) in eukaryotic cells. It comprises the following functional elements:

an origin of replication derived from the vector pUC18 (pUC origin),
a ß(beta)-lactamase gene conferring ampicillin resistance in E. coli (Amp),
an expression cassette for the expression of the gamma 1-heavy chain comprising the following elements:
  the major immediate-early promoter and enhancer from the human cytomegalovirus (hCMV IE1 promoter),
  a synthetic 5'UTR including a Kozak sequence,
  a murine immunoglobulin heavy chain signal sequence including the signal sequence intron (L1_Intron_L2),
  the cDNA for the heavy chain variable region (VH) arranged with a splice donor site at the 3' end,
  the mouse immunoglobulin µ-enhancer region,
  the human immunoglobulin heavy chain gamma 1-gene (IGHG1) including exons CH1, Hinge, CH2 and CH3, intervening introns and the 3'UTR bearing the polyadenylation signal sequence,
an expression cassette for the expression of the kappa-light chain comprising the following elements:
  the major immediate-early promoter and enhancer from the human cytomegalovirus (hCMV IE1 promoter),
  a synthetic 5'UTR including a Kozak sequence,
  a murine immunoglobulin heavy chain signal sequence including the signal sequence intron (L1_Intron_L2),
  the cDNA for the light chain variable region arranged with a splice donor site at the 3' end (VL),
  the intronic mouse Ig-kappa enhancer region,
  the human immunoglobulin kappa gene (IGK) including the IGKC exon and the IGK 3'UTR bearing the polyadenylation signal sequence,
an expression cassette for the expression of murine dihydrofolate reductase (DHFR) suitable for auxotrophic selection in eukaryotic cells including
  a shortened version of the SV40 early promoter and origin,
  the coding sequence for murine DHFR,
  the SV40 early polyadenylation signal.

P6454 was transfected into CHO-K1 cells and stable cell lines were isolated after selection with methotrexate (MTX) and were screened for production of humanized antibody by ELISA for human IgG.

Example 3

Inhibition of IL-17A Mediated Stimulation of Primary Normal Human Dermal Fibroblasts In-Vitro Normal human dermal fibroblasts (NHDF) cells produce hIL-6 in response to IL-17 stimulation. The assay is performed to measure the inhibition of this IL-17 stimulated cytokine production by NHDF cells following pre-incubation of the cells with anti-IL17 antibody in-vitro.

NHDF cells were cultured in Fibroblast Growth Medium-2 (Cambrex, #CC 3132) at a density of $4\times10^5$ cells/ml in a volume of 0.5 ml per well in a 48-well plate. NHDF cells were incubated overnight at 37° C. and 5% $CO_2$ to adhere. After overnight incubation, the media was aspirated off and replaced with 300 µl fresh media, cells were then treated with the antibody for 30 minutes across a range of antibody concentrations (3000, 1000, 300, 100, 30, 10, 3, 1, 0 ng/ml). The antibody dilution series was made with medium using 100 µl/well (5× concentrated). After 30 min. pre-incubation with the antibody, the cells were stimulated with 10 ng/ml hIL-17 (100 µl of 50 ng/ml 5× concentration, R&D Systems #317-IL) and incubated overnight (18 h) at 37° C. and 5% $CO_2$. For unstimulated controls, 100 µl of media was used (with and without antibodies present). After the incubation period, supernatants were transferred into fresh tubes and either analyzed immediately or stored at −80° C. until analysis by ELISA.

Example 4

Human IL6 ELISA hIL-6 ELISA (BD Biosciences #555220) was used according to the manufacturer's instructions to measure hIL-6 levels in the culture supernatants to assess the potency of antibodies at inhibiting IL-17 induced hIL-6.

100 µl diluted capture antibody (diluted 1:250 in coating buffer) was added to each well of a 96 well Nunc MaxiSorp plate (Nunc #456537) and incubated overnight at 4° C. Plates were aspirated, washed three times with wash buffer, blocked with 200 µl/well assay diluent for 1 hour at room temperature. Plates were aspirated, washed three times with wash buffer, then 100 µl of standards and assay samples were added according to the manufactures instructions and incubated for 2 h at room temperature. Plates were aspirated, washed at least three times with wash buffer. 100 µl conjugate (detection antibody+enzyme, diluted 1:250 in assay diluent) was added to each well and incubated for 1 hour at room temperature. Plates were aspirated, washed at least five times with wash buffer. 100 µl TMB substrate was added to each well and incubated until sufficient color had developed for reading. The reaction was stopped with 50 µl/well 1 M $H_2SO_4$ and read on the plate reader at a wavelength of 450 nm within 30 minutes.

Example 5

Surface Plasmon Resonance-Based Assay (SPR-Based Assay)

All measurements were performed using the BIAcore 3000 instrument at 25° C. The system and sample buffer was HBS-EP (10 mM HEPES, 150 mM NaCl, 3.4 mM EDTA, 0.005% Polysorbate 20 (v/v)). A BIAcore CM5 sensor chip was subjected to a preconditioning procedure. Sequentially 0.1% SDS, 50 mM NaOH, 10 mM HCl and 100 mM H3P04 was injected for 30 sec. over the flow cells.

The amine coupling procedure was done according to the manufacturer's instructions using the BIAcore 3000 wizard v. 4.1. After an EDC/NHS activation of the sensor surface a polyclonal goat anti-human IgG antibody (Jackson) was immobilized on all sensor flow cells (FCs). 30 µg/ml polyclonal goat anti-human IgG antibody in 10 mM NaAc pH 5.0 was used at 10 µl/min for 7 min. to immobilize about 10,000 RU of the antibody capturing system. The surface was deactivated by saturation with ethanolamine. The human capture system sensor was conditioned with 5 cycles of binding of huIgG analyte (Bayer) at 10 µl/min for 2 min and regeneration with 10 mM glycine pH 1.7 at 30 µl/min for 3 min.

Second, the antibody was injected to form the capture system.

Third, the antigen was injected within a defined concentration range. The binding responses (resonance units, RU) obtained after injection of the antigen correlate with the amount of antigen bound to the antibody and were plotted against the antigen concentration range used. The resulting linear plot was analyzed by appropriate computer software (e.g. XLfit4, IDBS Software), which fits a 2-parametric line and hence allows determination of the y-axis intercept as the biological activity readout.

The invention claimed is:

1. A method for producing a nucleic acid sequence encoding a humanized immunoglobulin variable domain, comprising the steps of:
   a) aligning the amino acid sequence of a non-human heavy chain or light chain variable domain
      with
      a first humanized variant of said non-human heavy chain or light chain variable domain obtained by grafting the CDRs or hypervariable regions or specificity determining residues of the respective non-human antibody heavy chain or light chain variable domain on
         i) a human germline amino acid sequence with the highest sequence homology to the non-human variable domain,
         or
         ii) two or more human germline amino acid sequence fragments that when aligned have a homology higher than a single human germline amino acid sequence,
         or
         iii) a human germline amino acid sequence that allows maintaining VH/VL angle
      with maximal level of amino acid sequence identity,
   b) identifying aligned framework positions in which the non-human heavy chain or light chain variable domain and the first humanized variant of said non-human heavy chain or light chain variable domain have different amino acid residues, which, due to the difference, influence antigen binding and/or three dimensional structure of the variable domain in combination with the respective other variable domain as Fv, c) modifying the first humanized variant of said non-human heavy chain or light chain variable domain by replacing one or more amino acid residue identified in step b) with an amino acid residue that influences antigen binding directly and/or the three dimensional structure of the variable domain in combination with the respective other variable domain as Fv less than the replaced amino acid residue, and d) producing a nucleic acid sequence encoding the modified variable domain and thereby producing a nucleic acid sequence encoding a humanized immunoglobulin variable domain, wherein:

step b) further comprises the assigning to all amino acid residues one of the topology classifiers I (internal side chain), E (external side chain), C (contact heavy-light chains), A (antigen contact), or S (participating in salt bridge), step b) further comprises assigning a score of 0, 1, 2, 3 or 4 to each difference, and a score of 0 is assigned to a change of an amino acid residue with the topology E to any amino acid residue except proline and a change to proline is assigned a score of 3 or 4, a score of 0 is assigned to a change of an amino acid residue with the topology I to an amino acid residue with a smaller side chain, the replacement with an amino acid residue with a side chain that has one carbon atom more will be assigned a score of 1, the replacement with an amino acid residue with a side chain that has two carbon atoms more will be assigned a score of 2, the replacement with an amino acid residue with a side chain that has three carbon atoms more will be assigned a score of 3, and all other changes will be assigned a score of 4, a score of 4 is assigned to a change of an amino acid residue with the topology A to any amino acid residue, a score of 3 is assigned to the change of an amino acid residue with the topology C to a non-hydrophobic amino acid residue, and a score of 3 is assigned to a change of an amino acid residue with the topology S to an oppositely charged or not-charged amino acid residue if the salt bridge is solvent exposed and a score of 4 is assigned if the salt bridge is internal.

2. The method according to claim 1, wherein step b) further comprises the generation of a three-dimensional model of the non-human variable domains or the non-human antibody using homology modeling.

* * * * *